United States Patent
Sims

(10) Patent No.: US 8,231,887 B2
(45) Date of Patent: Jul. 31, 2012

(54) PESTICIDAL COMPOSITIONS

(75) Inventor: Steven R. Sims, St. Louis, MO (US)

(73) Assignee: BASF Corporation, Florham Park, NJ (US)

( * ) Notice: Subject to any disclaimer, the term of this patent is extended or adjusted under 35 U.S.C. 154(b) by 464 days.

(21) Appl. No.: 12/418,443

(22) Filed: Apr. 3, 2009

(65) Prior Publication Data

US 2009/0257958 A1  Oct. 15, 2009

Related U.S. Application Data

(60) Provisional application No. 61/044,297, filed on Apr. 11, 2008, provisional application No. 61/115,231, filed on Nov. 17, 2008.

(51) Int. Cl.
*A01N 25/00* (2006.01)

(52) U.S. Cl. .................... 424/405; 514/529; 525/13

(58) Field of Classification Search .................. 424/405; 514/529; 525/13
See application file for complete search history.

(56) References Cited

U.S. PATENT DOCUMENTS

| | | | |
|---|---|---|---|
| 2,763,614 A | 9/1956 | Cantrell et al. | |
| 3,163,607 A | 12/1964 | Drake et al. | |
| 3,806,593 A * | 4/1974 | Swanbeck et al. | 424/401 |
| 4,056,610 A | 11/1977 | Barber, Jr. et al. | |
| 4,252,796 A * | 2/1981 | Yu et al. | 514/181 |
| 4,285,868 A | 8/1981 | Heiba et al. | |
| 4,534,128 A | 8/1985 | Query et al. | |
| 4,562,214 A * | 12/1985 | Barker et al. | 514/769 |
| 4,612,331 A * | 9/1986 | Barratt et al. | 514/558 |
| 4,624,070 A | 11/1986 | Query et al. | |
| 4,774,081 A | 9/1988 | Flashinski et al. | |
| 4,774,082 A | 9/1988 | Flashinski et al. | |
| 4,822,614 A | 4/1989 | Rodero | |
| 4,902,510 A | 2/1990 | Garden | |
| 4,923,698 A | 5/1990 | Rodero | |
| 4,933,371 A | 6/1990 | Hink et al. | |
| 4,961,532 A | 10/1990 | Tangney | |
| 4,962,133 A | 10/1990 | Chromecek et al. | |
| 5,093,326 A | 3/1992 | Herman | |
| 5,143,900 A | 9/1992 | Steltenkamp et al. | |
| 5,227,163 A | 7/1993 | Eini et al. | |
| 5,227,406 A | 7/1993 | Beldock et al. | |
| 5,290,556 A | 3/1994 | McKibben et al. | |
| 5,344,776 A | 9/1994 | Venter et al. | |
| 5,346,922 A | 9/1994 | Beldock et al. | |
| 5,411,992 A | 5/1995 | Eini et al. | |
| 5,435,992 A | 7/1995 | Audegond et al. | |
| 5,476,609 A | 12/1995 | Wilkins, Jr. et al. | |
| 5,510,117 A | 4/1996 | Abate | |
| 5,525,597 A | 6/1996 | Hainrihar et al. | |
| 5,536,501 A | 7/1996 | Emerson et al. | |
| 5,538,990 A | 7/1996 | Banks et al. | |
| 5,559,271 A | 9/1996 | Shaw et al. | |
| 5,562,864 A | 10/1996 | Salomon et al. | |
| 5,599,803 A | 2/1997 | Hainrihar et al. | |
| 5,621,013 A | 4/1997 | Beldock et al. | |
| 5,648,398 A | 7/1997 | Beldock et al. | |
| 5,654,362 A | 8/1997 | Schulz, Jr. et al. | |
| 5,674,518 A | 10/1997 | Fajt | |
| 5,679,662 A | 10/1997 | Chang et al. | |
| 5,698,210 A | 12/1997 | Levy | |
| 5,753,507 A | 5/1998 | Ohta et al. | |
| 5,753,686 A | 5/1998 | Marin et al. | |
| 5,792,465 A | 8/1998 | Hagarty | |
| 5,814,325 A | 9/1998 | Rod | |
| 5,834,413 A | 11/1998 | Durbut et al. | |
| 5,834,533 A | 11/1998 | Patel et al. | |
| 5,872,143 A | 2/1999 | Tanaka et al. | |
| 5,880,210 A | 3/1999 | Schulz, Jr. et al. | |
| 5,902,596 A | 5/1999 | Levy | |
| 5,925,182 A | 7/1999 | Patel et al. | |
| 5,977,023 A | 11/1999 | Inoue et al. | |
| 5,977,186 A | 11/1999 | Franklin | |
| 5,998,484 A | 12/1999 | Zobitne et al. | |
| 6,001,874 A | 12/1999 | Veierov | |
| 6,024,972 A | 2/2000 | Narayanan et al. | |
| 6,071,857 A | 6/2000 | Vogt et al. | |
| 6,074,634 A | 6/2000 | Lopez, Jr. et al. | |
| 6,124,490 A | 9/2000 | Gormley et al. | |
| 6,130,253 A | 10/2000 | Franklin et al. | |
| 6,184,197 B1 | 2/2001 | Heinzman et al. | |
| 6,197,098 B1 | 3/2001 | Narayanan et al. | |
| 6,251,415 B1 | 6/2001 | Herbert | |
| 6,255,350 B1 | 7/2001 | Jon et al. | |
| 6,255,356 B1 | 7/2001 | Butler | |
| 6,277,415 B1 | 8/2001 | Levin et al. | |

(Continued)

FOREIGN PATENT DOCUMENTS

| | | |
|---|---|---|
| CA | 2644273 A1 | 3/2008 |
| CN | 1481849 A | 3/2004 |
| EP | 0417606 A2 | 3/1991 |
| EP | 0417606 B1 | 4/1995 |
| EP | 0646314 A1 | 4/1995 |
| EP | 0869142 A2 | 10/1998 |
| EP | 0925717 A1 | 6/1999 |

(Continued)

OTHER PUBLICATIONS

Ergon, "Hyvolt I", Oct. 1, 2009, pp. 1-6.*
International Search Report and Written Opinion for PCT/US09/39664, dated Jan. 12, 2010, 11 pages.
Viyoch et al., "Evaluation of in vitro antimicrobial activity of Thai basil oils and their micro-emulsion formulas against Propionibacterium acnes," International Journal of Cosmetic Science, vol. 28, No. 2 (2004), pp. 125-133 (Abstract Only).
"Geraniol" from Wikipedia Free Encyclopedia, http://en.wikipedia.org/wiki/Geraniol, 2 pages, printed Feb. 19, 2009.

(Continued)

*Primary Examiner* — Anoop Singh
*Assistant Examiner* — Ali Soroush
(74) *Attorney, Agent, or Firm* — Armstrong Teasdale LLP

(57) ABSTRACT

The present disclosure relates to pesticidal compositions and to methods for controlling pests such as insects and other arthropods. More particularly, the disclosure relates to a pesticidal compositions containing mineral oil and one or more additional components which, when used in combination, act synergistically to control insect and pest populations.

10 Claims, 2 Drawing Sheets

U.S. PATENT DOCUMENTS

| | | |
|---|---|---|
| 6,306,416 B1 | 10/2001 | McKibben et al. |
| 6,313,073 B1 | 11/2001 | Farooqi et al. |
| 6,316,017 B1 | 11/2001 | McKibben et al. |
| 6,337,078 B1 | 1/2002 | Levy |
| 6,344,208 B1 | 2/2002 | Howse |
| 6,346,262 B1 | 2/2002 | Levy |
| 6,355,264 B1 | 3/2002 | Garrison et al. |
| 6,441,051 B1 | 8/2002 | Wheeler |
| 6,447,795 B2 | 9/2002 | Kalder et al. |
| 6,455,086 B1 | 9/2002 | Trinh et al. |
| RE37,890 E | 10/2002 | Levy |
| 6,482,455 B1 | 11/2002 | Freire et al. |
| 6,514,511 B1 | 2/2003 | Thoenes |
| 6,555,121 B1 | 4/2003 | Bessette et al. |
| 6,592,637 B2 | 7/2003 | McGee et al. |
| 6,607,716 B1 | 8/2003 | Smith et al. |
| 6,641,803 B1 * | 11/2003 | Kahre et al. ................ 424/70.1 |
| 6,673,756 B2 | 1/2004 | Sonnenberg et al. |
| 6,689,395 B2 | 2/2004 | Bessette |
| 6,706,760 B2 | 3/2004 | Matsunaga |
| 6,749,861 B2 | 6/2004 | Mullen |
| 6,773,700 B2 | 8/2004 | Thoenes |
| 6,774,113 B2 | 8/2004 | Bertho et al. |
| 6,811,772 B2 | 11/2004 | Thoenes |
| 6,849,614 B1 | 2/2005 | Bessette et al. |
| 6,877,271 B2 | 4/2005 | Hughes et al. |
| 6,881,776 B2 | 4/2005 | Butuc |
| 6,969,522 B2 | 11/2005 | Bessette |
| 6,974,584 B2 | 12/2005 | Bessette |
| 7,081,211 B2 | 7/2006 | Li et al. |
| RE39,543 E | 4/2007 | Emerson et al. |
| 7,201,926 B2 | 4/2007 | Fried et al. |
| 7,250,175 B2 | 7/2007 | Bessette et al. |
| 7,282,211 B2 | 10/2007 | Ping |
| 7,320,966 B2 | 1/2008 | Bessette et al. |
| 7,351,420 B2 | 4/2008 | Bessette et al. |
| 7,361,366 B2 | 4/2008 | Bessette et al. |
| 7,368,613 B2 | 5/2008 | Eh |
| 7,465,469 B2 | 12/2008 | Ben-Yehoshua |
| 2001/0055604 A1 | 12/2001 | Kalder et al. |
| 2002/0028256 A1 | 3/2002 | Bessette |
| 2002/0055562 A1 | 5/2002 | Butuc |
| 2002/0085979 A1 | 7/2002 | Matsunaga |
| 2002/0099187 A1 | 7/2002 | Bertho et al. |
| 2002/0168600 A1 | 11/2002 | McGee et al. |
| 2002/0193250 A1 | 12/2002 | Bessette |
| 2002/0193346 A1 | 12/2002 | Greeson et al. |
| 2003/0017178 A1 | 1/2003 | Mullen |
| 2003/0036530 A1 | 2/2003 | Bessette |
| 2003/0039674 A1 | 2/2003 | Bessette |
| 2003/0060379 A1 | 3/2003 | Souter et al. |
| 2003/0091661 A1 | 5/2003 | Bessette |
| 2003/0105192 A1 | 6/2003 | Li et al. |
| 2003/0147933 A1 | 8/2003 | Thoenes |
| 2003/0165452 A1 | 9/2003 | Gonzalez et al. |
| 2003/0170283 A1 | 9/2003 | Thoenes |
| 2003/0175369 A1 | 9/2003 | Khazan-Enache |
| 2003/0194454 A1 | 10/2003 | Bessette et al. |
| 2003/0228342 A1 | 12/2003 | Ping |
| 2004/0000660 A1 | 1/2004 | Li |
| 2004/0047889 A1 | 3/2004 | Greeson et al. |
| 2004/0154214 A1 | 8/2004 | Hughes et al. |
| 2004/0220075 A1 | 11/2004 | Ahrens |
| 2004/0234662 A1 | 11/2004 | Ben-Yehoshua |
| 2004/0248764 A1 | 12/2004 | Franklin |
| 2004/0253287 A1 | 12/2004 | Denton |
| 2004/0259732 A1 | 12/2004 | Asrar et al. |
| 2005/0002980 A1 | 1/2005 | Mullen |
| 2005/0004274 A1 | 1/2005 | Healy et al. |
| 2005/0008714 A1 | 1/2005 | Enan |
| 2005/0136089 A1 | 6/2005 | Bessette et al. |
| 2005/0170025 A1 | 8/2005 | Bessette et al. |
| 2005/0214267 A1 | 9/2005 | Enan |
| 2005/0232981 A1 | 10/2005 | Ben-Sasson |
| 2005/0244445 A1 | 11/2005 | Anderson |
| 2005/0260241 A1 | 11/2005 | Bessette et al. |
| 2005/0261379 A1 | 11/2005 | Fefer |
| 2006/0014724 A1 | 1/2006 | Jadhav et al. |
| 2006/0034898 A1 | 2/2006 | Amodt et al. |
| 2006/0083763 A1 | 4/2006 | Neale et al. |
| 2006/0115508 A1 | 6/2006 | Bessette |
| 2006/0116353 A1 | 6/2006 | Vanmoor |
| 2006/0121073 A1 | 6/2006 | Goyal et al. |
| 2006/0193789 A1 | 8/2006 | Tamarkin et al. |
| 2006/0211575 A1 | 9/2006 | Sedun et al. |
| 2006/0222675 A1 | 10/2006 | Sabinis et al. |
| 2006/0263403 A1 | 11/2006 | Enan |
| 2007/0020304 A1 | 1/2007 | Tamarkin et al. |
| 2007/0071784 A1 | 3/2007 | Rakoczi et al. |
| 2007/0071785 A1 | 3/2007 | Craven et al. |
| 2007/0093551 A1 | 4/2007 | Yu et al. |
| 2007/0098750 A1 | 5/2007 | Bessette |
| 2007/0148204 A1 | 6/2007 | Parker et al. |
| 2007/0166342 A1 | 7/2007 | Darling |
| 2007/0178128 A1 | 8/2007 | Bessette |
| 2007/0190094 A1 | 8/2007 | Bessette |
| 2007/0207221 A1 | 9/2007 | Bessette et al. |
| 2007/0244121 A1 | 10/2007 | Walter et al. |
| 2007/0251020 A1 | 11/2007 | Stockman et al. |
| 2007/0298131 A1 | 12/2007 | Bessette et al. |
| 2007/0299037 A1 | 12/2007 | Bessette et al. |
| 2007/0299038 A1 | 12/2007 | Bessette et al. |
| 2008/0003315 A1 | 1/2008 | Bessette et al. |
| 2008/0003316 A1 | 1/2008 | Bessette et al. |
| 2008/0003317 A1 | 1/2008 | Bassette et al. |
| 2008/0004240 A1 | 1/2008 | Bessette et al. |
| 2008/0015167 A1 | 1/2008 | Bessette et al. |
| 2008/0015262 A1 | 1/2008 | Ping |
| 2008/0020078 A1 | 1/2008 | Enan |
| 2008/0038383 A1 | 2/2008 | Bessette et al. |
| 2008/0044375 A1 | 2/2008 | McKibben |
| 2008/0047312 A1 | 2/2008 | Hill et al. |
| 2008/0070785 A1 | 3/2008 | Walter et al. |
| 2008/0075796 A1 | 3/2008 | Enan |
| 2008/0076664 A1 | 3/2008 | Walter et al. |
| 2008/0076699 A1 | 3/2008 | Ley et al. |
| 2008/0118585 A1 | 5/2008 | Nouvel |
| 2008/0132583 A1 | 6/2008 | Friend et al. |
| 2008/0159970 A1 | 7/2008 | Willemin |
| 2008/0181968 A1 | 7/2008 | Besendorfer |
| 2008/0187607 A1 | 8/2008 | Bessette |
| 2008/0193387 A1 | 8/2008 | DeWolff |
| 2008/0207448 A1 | 8/2008 | Marx et al. |
| 2008/0213198 A1 | 9/2008 | Lintner et al. |
| 2008/0248120 A1 | 10/2008 | Anderson et al. |
| 2008/0271761 A1 | 11/2008 | Sherrel et al. |

FOREIGN PATENT DOCUMENTS

| | | |
|---|---|---|
| EP | 1256336 A2 | 11/2002 |
| EP | 1224239 B1 | 5/2003 |
| EP | 0646314 B1 | 8/2004 |
| EP | 0869142 B1 | 12/2004 |
| EP | 0991327 B1 | 12/2004 |
| EP | 1141111 B1 | 8/2005 |
| EP | 0925717 B1 | 10/2008 |
| WO | 9900025 A1 | 1/1999 |
| WO | 9921891 A1 | 5/1999 |
| WO | 0026285 A1 | 5/2000 |
| WO | 0118201 A1 | 3/2001 |
| WO | 2005102266 A1 | 11/2005 |
| WO | 2006105193 A2 | 10/2006 |
| WO | 2007052016 A2 | 5/2007 |
| WO | 2007056340 A2 | 5/2007 |
| WO | 2007068998 A1 | 6/2007 |
| WO | 2007093839 A1 | 8/2007 |
| WO | 2007146114 A2 | 12/2007 |
| WO | 2008011054 A2 | 1/2008 |
| WO | 2008034648 A1 | 3/2008 |
| WO | 2008048963 A2 | 4/2008 |
| WO | 2008056365 A2 | 5/2008 |
| WO | 2008088827 A2 | 7/2008 |
| WO | 2008101131 A1 | 8/2008 |
| WO | 2008123574 A2 | 10/2008 |
| WO | 2009012415 A1 | 1/2009 |

OTHER PUBLICATIONS

"Isopropyl Myristate" from Wikipedia Free Encyclopedia, http://en.wikipedia.org/wiki/Isopropyl_myristate, 2 pages, printed Feb. 19, 2009.
Co-owned U.S. Appl. No. 12/418,455, filed Apr. 3, 2009.
Co-owned U.S. Appl. No. 12/418,466, filed Apr. 3, 2009.
Office Action mailed Aug. 3, 2011 for Co-Owned U.S. Appl. No. 12/418,455.
Final Office Action mailed May 13, 2011 for Co-Owned U.S. Appl. No. 12/418,466.
Office Action mailed Dec. 8, 2010 for Co-Owned U.S. Appl. No. 12/418,466.
Office Action dated Feb. 3, 2012 cited in related U.S. Appl. No. 12/418,455, filed Apr. 3, 2009, 10 pages.
Extended Search Report for European Application No. 09730159.2-2103, dated Mar. 6, 2012, 5 pages.

* cited by examiner

PESTICIDAL COMPOSITIONS

CROSS-REFERENCE TO RELATED APPLICATIONS

This application claims the benefit of U.S. Provisional Application No. 61/044,297 filed Apr. 11, 2008 and U.S. Provisional Application No. 61/115,231, filed Nov. 17, 2008.

BACKGROUND OF THE DISCLOSURE

The present disclosure relates to pesticidal compositions and a method of controlling insects and other pests. More particularly, the disclosure relates to pesticidal compositions containing mineral oil and one or more additional components which, when used in combination, act synergistically to control pests such as arthropods.

Insects and other arthropod pests can have negative effects on the quality of human life. For instance, when found in the home, insects and other arthropods can be a source of annoyance due purely to their presence. They may also spread disease and allergens. Additionally, when found on plants and crops, insects and other pest arthropods can destroy foliage and fruit, and may adversely affect plant and crop growth, quality, and yield.

Among the insects which are particularly undesirable are domestic cockroaches. These insects produce allergens in their saliva, fecal material, cast skins and body parts which may be particularly problematic for people suffering from allergies.

It is domestically and commercially desirable to control cockroaches through the use of pesticide products. It is also desirable for to control other crawling arthropods, such as ants, beetles, earwigs, silverfish, crickets, spiders, centipedes and various flying insects including flies, mosquitoes, gnats, moths, wasps, hornets, bees, and the like.

A broad range of compounds have been found to be toxic to insects and other arthropods such that formulations containing the compounds may be used for their control. However, most compounds damage the environment and adversely affect human health. There is a need for new pesticides which are generally safe to the environment and non-toxic to humans and animals and which are effective at controlling insect and other pest populations.

SUMMARY OF THE DISCLOSURE

The present disclosure relates to pesticidal compositions and a method of controlling pests such as arthropods and, in particular, insects. The pesticidal compositions of embodiments of the present disclosure are particularly effective at controlling cockroaches. More particularly, the disclosure relates to a pesticidal composition containing mineral oil and one or more additional components which, when used in combination, act synergistically to control insect and other pest populations.

In one aspect, the present disclosure is directed to a pesticidal composition comprising a first active ingredient and a second active ingredient. The first active ingredient is a mineral oil and the second active ingredient is an ester compound. The ester compound is selected from the group consisting of ethyl lactate, γ-butyrolactone, triacetin and combinations thereof.

In another aspect, the pesticidal composition comprises a first active ingredient and a second active ingredient. The first active ingredient is a mineral oil and the second active ingredient is an alcohol selected from the group consisting of methanol, 1-proponal, 1-butanol, 1-hexanol, 1-heptanol, 1-octanol, 1-nonanol, 1-decanol, 1-undecanol, 1-dodecanol, 1-tetradecanol, 2-butanol, isobutyl alcohol, tertiary butyl alcohol, 2-butoxyethanol, 2-phenylethanol, diacetone alcohol, 2-ethoxyethanol and combinations thereof.

In yet another aspect, the pesticidal composition comprises a first active ingredient and a second active ingredient. The first active ingredient is a mineral oil and the second active ingredient is selected from the group consisting of hexylene glycol, dioxane, nitromethane, acetophenone, pyridine and combinations thereof.

In another aspect, the present disclosure is directed to a method of controlling arthropods. An arthropod is contacted with a pesticidally effective amount of a composition comprising a first active ingredient and a second active ingredient. The first active ingredient is a mineral oil and the second active ingredient is an ester compound.

In a further aspect of the method, an arthropod is contacted with a pesticidally effective amount of a composition comprising a first active ingredient and a second active ingredient. The first active ingredient is a mineral oil and the second active ingredient is an alcohol selected from the group consisting of methanol, 1-proponal, 1-butanol, 1-hexanol, 1-heptanol, 1-octanol, 1-nonanol, 1-decanol, 1-undecanol, 1-dodecanol, 1-tetradecanol, 2-butanol, isobutyl alcohol, tertiary butyl alcohol, 2-butoxyethanol, 2-phenylethanol, diacetone alcohol, 2-ethoxyethanol and combinations thereof.

In yet another aspect of the method, the arthropod is contacted with a pesticidally effective amount of a composition comprising a first active ingredient and a second active ingredient. The first active ingredient is a mineral oil and the second active ingredient is selected from the group consisting of hexylene glycol, dioxane, d-limonene, nitromethane, acetophenone, pyridine and combinations thereof.

A further aspect of the present disclosure is directed to a method of controlling cockroaches. A cockroach is contacted with a pesticidally effective amount of a composition comprising a first active ingredient and at least 3% of a second active ingredient by weight of the composition. The first active ingredient is a mineral oil and the second active ingredient is an alcohol.

Other objects and features will be in part apparent and in part pointed out hereinafter.

DETAILED DESCRIPTION OF THE DISCLOSURE

Figure 1:
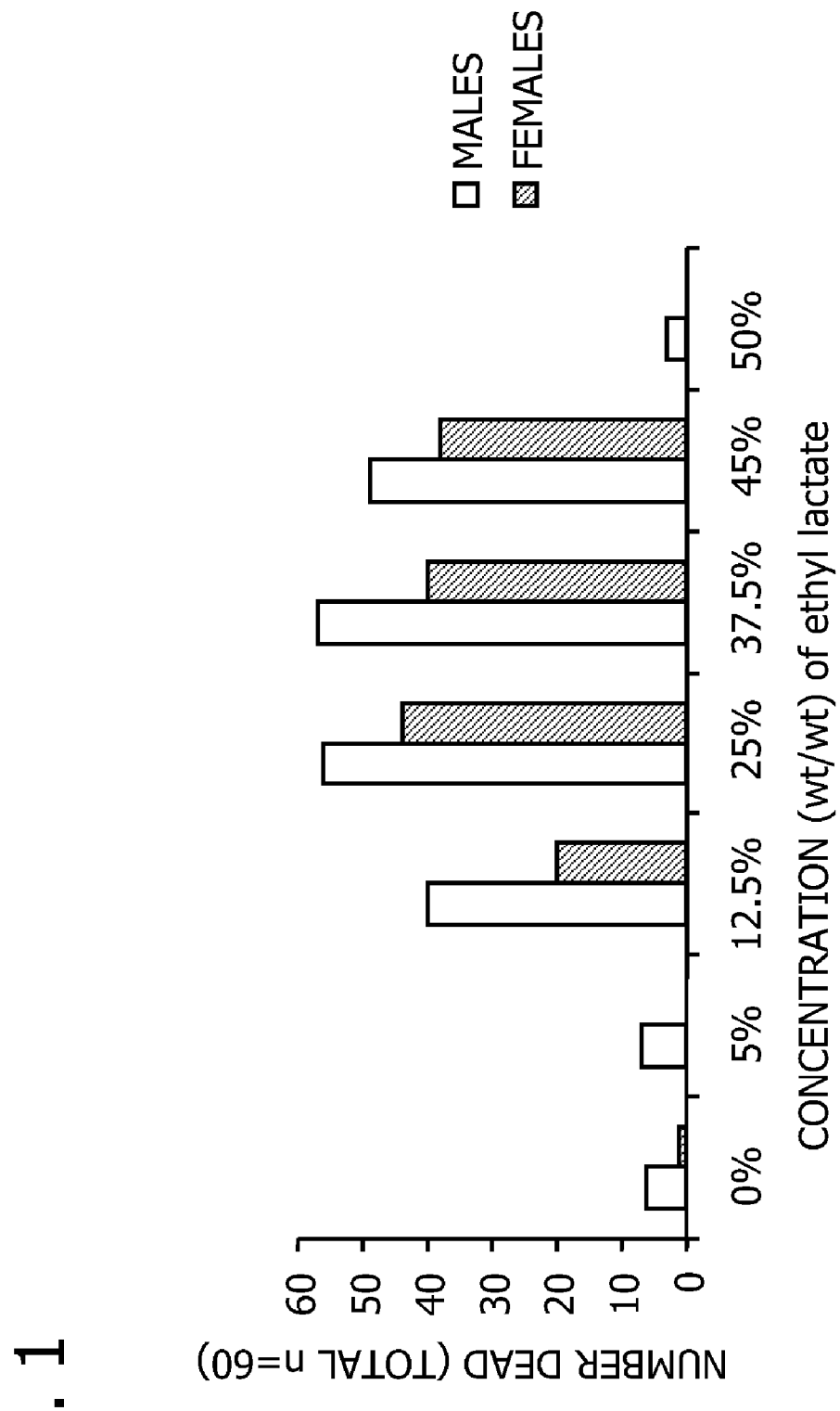
FIG. 1 is a chart depicting the effects of compositions comprising mineral oil and/or ethyl lactate on the mortality of adult German cockroaches as discussed in Example 1.

In accordance with the present disclosure, it has now been found that the combination of mineral oil and one or more additional compounds selected from the group consisting of ethyl lactate, butyl lactate, isopropyl myristate, hexylene glycol, dioxane, d-limonene, a C1-C14 saturated straight-chain alcohol, isopropyl alcohol, 2-butanol, isobutyl alcohol, tertiary butyl alcohol, 2-butoxyethanol, 2-phenylethanol, diacetone alcohol, and combinations thereof, is effective for use in controlling insect and other pest populations. In particular, it has been discovered that compositions comprising mineral oil in combination with ethyl lactate, butyl lactate, isopropyl myristate, hexylene glycol, dioxane, d-limonene, a C1-C14 saturated straight-chain alcohol, isopropyl alcohol, 2-butanol, isobutyl alcohol, tertiary butyl alcohol, 2-butoxyethanol, 2-phenylethanol, diacetone alcohol, γ-butyrolactone, nitromethane, acetophenone, triacetin, pyridine, 2-ethoxyethanol or combinations thereof are more effective at killing targeted insects and pests than compositions comprising only mineral oil or compositions comprising ethyl lactate, butyl lactate, isopropyl myristate, hexylene glycol, dioxane, d-limonene, a C1-C14 saturated straight-chain alcohol, isopropyl alcohol, 2-butanol, isobutyl alcohol, tertiary butyl alcohol, 2-butoxyethanol, 2-phenylethanol, diacetone alcohol, γ-butyrolactone, nitromethane, acetophenone, triacetin, pyridine, or 2-ethoxyethanol but no mineral oil. Advantageously, the compositions of the present disclosure also have a generally lower or reduced non-target (e.g., humans, other mammals, birds and reptiles) toxicity as compared to many other known pest control materials.

Thus, in one aspect, the present disclosure is directed to a pesticidal composition comprising a first active ingredient and a second active ingredient, the first active ingredient being mineral oil, and the second active ingredient being selected from the group consisting of ethyl lactate, butyl lactate, isopropyl myristate, hexylene glycol, dioxane, d-limonene, a C1-C14 saturated straight-chain alcohol, isopropyl alcohol, 2-butanol, isobutyl alcohol, tertiary butyl alcohol, 2-butoxyethanol, 2-phenylethanol, diacetone alcohol, γ-butyrolactone, nitromethane, acetophenone, triacetin, pyridine, 2-ethoxyethanol and combinations thereof. The composition may be sprayed or otherwise applied directly on crawling or flying insects or other arthropod pests in sufficient concentrations to kill the pests.

As noted above, the pesticidal compositions of the present disclosure comprise a first active ingredient which is mineral oil. Any type of mineral oil may be used in the pesticidal compositions. In one preferred embodiment, the mineral oil is PD-23 (available from Chemtura Corporation, Middlebury, Conn.). PD-23 is a light grade petroleum distillate having a flash point of 230° F. (110° C.), as measured by ASTM D-92, and a vapor pressure of less than 0.1 mmHg at 20° C. PD-23 is a highly refined petroleum distillate that physically resembles a very light, clear oil, and is made by fractionating oil to a narrow boiling range, then catalytically hydrotreating it to remove all aromatic and other unsaturated hydrocarbons. PD-23 is hydrophobic, colorless, tasteless, virtually odorless, and color fast. PD-23 generally has a low viscosity, e.g., about 2.6 centistokes (cSt) at 40° C. or a Saybolt Universal Seconds (SUS) viscosity of about 34 SUS at 100° F. (38° C.).

Other types of suitable mineral oils may also be used including, for example, PD-25 and PD-28 (both available from Chemtura Corporation, Middlebury, Conn.). PD-25 typically has a viscosity of about 3.5 cSt at 40° C. or about 39 SUS at 100° F. (38° C.). PD-28 typically has a viscosity of about 4.2 cSt at 40° C. or about 39 SUS at 100° F. (38° C.). Another suitable mineral oil is EXXSOL D95 (available from Exxon Mobil). EXXSOL D95 is a de-aromatized petroleum distillate. EXXSOL D95 typically has a viscosity of about 1.92 cSt at 40° C.

Typically, the viscosity of the mineral oil will range from about 2.0 cSt at 40° C. to about 5.0 cSt at 40° C., and more typically will be from about 2.6 cSt at 40° C. to about 4.2 cSt at 40° C. In other embodiments the viscosity of the mineral oil is from about 1.5 cSt to about 5.0 cSt at 40° C. In general, it has been determined that pesticidal compositions of the present disclosure that comprise a mineral oil having a relatively low viscosity are more effective at killing pests than pesticidal compositions comprising mineral oil having a higher viscosity.

In one embodiment, the pesticidal composition comprises more than one mineral oil. The total amount of mineral oil present in the pesticidal composition may be at least about 5% (by weight of the composition), at least about 10% (by weight of the composition), at least about 20% (by weight of the composition), at least about 30% (by weight of the composition), at least about 40% (by weight of the composition), or even at least about 50% (by weight of the composition).

Typically, the pesticidal compositions will comprise from about 5% (by weight of the composition) to about 90% (by weight of the composition) of mineral oil, and more typically from about 40% (by weight of the composition) to about 80% (by weight of the composition) of mineral oil.

In some embodiments, the mineral oil is a petroleum distillate composition. The amount of petroleum distillate composition in the pesticidal composition may generally be the same as the amounts listed for the mineral oil as described above.

In addition to mineral oil, the pesticidal compositions of the present disclosure further comprise at least one second active ingredient selected from the group consisting of ethyl lactate, butyl lactate, isopropyl myristate, hexylene glycol, dioxane, d-limonene, a C1-C14 saturated straight-chain alcohol, isopropyl alcohol, 2-butanol, isobutyl alcohol, tertiary butyl alcohol, 2-butoxyethanol, 2-phenylethanol, diacetone alcohol, γ-butyrolactone, nitromethane, acetophenone, triacetin, pyridine, 2-ethoxyethanol and combinations thereof. Advantageously, these second active ingredients act synergistically with mineral oil to provide a pesticidal composition that is effective in controlling insect and other pest populations. Surprisingly, as can be seen from the examples set forth hereinafter, compositions comprising a combination of mineral oil and one or more of ethyl lactate, butyl lactate, isopropyl myristate, hexylene glycol, dioxane, d-limonene, a C1-C14 saturated straight-chain alcohol, isopropyl alcohol, 2-butanol, isobutyl alcohol, tertiary butyl alcohol, 2-butoxyethanol, 2-phenylethanol and diacetone alcohol, γ-butyrolactone, nitromethane, acetophenone, triacetin, pyridine, 2-ethoxyethanol, are substantially more effective in killing insects than either mineral oil in the absence of one of these second active ingredients, or any of the second active ingredients in the absence of mineral oil.

In one embodiment, the pesticidal composition comprises more than one second active ingredient. The additional second active ingredient or ingredients may generally be selected from the list of compounds described above or below as potential second active ingredients.

The total amount of second active ingredient or ingredients present in the pesticidal composition may be at least about 3% (by weight of the composition), at least about 5% (by weight of the composition), at least about 10% (by weight of the composition), at least about 20% (by weight of the composition), at least about 30% (by weight of the composition), at least about 40% (by weight of the composition), or even at least about 50% (by weight of the composition).

The total amount of second active ingredient present in the pesticidal compositions will typically be from about 3% (by weight of the composition) to about 95% (by weight of the composition), more typically from about 5% (by weight of the composition) to about 95% (by weight of the composition), and more preferably from about 10% (by weight of the composition) to about 60% (by weight of the composition).

The amount of each particular second active ingredient present in the composition may vary depending on the ingredient, the amount of mineral oil in the composition, and whether or not more than one second active ingredient is present in the composition.

In one embodiment, the second active ingredient is selected from ethyl lactate, butyl lactate, isopropyl myristate, hexylene glycol, dioxane, d-limonene and combinations thereof. In another embodiment, the second active ingredient is selected from ethyl lactate, butyl lactate, isopropyl myristate, d-limonene and combinations thereof. In yet another embodiment, the second active ingredient is selected from the group consisting of ethyl lactate, isopropyl myristate, hexylene glycol, dioxane, d-limonene and combinations thereof and, in a further embodiment, ethyl lactate, isopropyl myristate, d-limonene and combinations thereof.

Typically, ethyl lactate may be present in the composition in an amount of from about 5% (by weight of the composition) to about 95% (by weight of the composition), and more preferably from about 10% (by weight of the composition) to about 60% (by weight of the composition). Compositions comprising about 12.5% (by weight of the composition) mineral oil and about 37.5% (by weight of the composition) ethyl lactate, or about 25% (by weight of the composition) mineral oil and about 25% (by weight of the composition) ethyl lactate, or about 37.5% (by weight of the composition) mineral oil and about 12.5% (by weight of the composition) ethyl lactate, or about 5% (by weight of the composition) mineral oil and about 45% (by weight of the composition) ethyl lactate have been found to be particularly effective at killing insects such as cockroaches.

Butyl lactate may be present in the composition in an amount of from about 5% (by weight of the composition) to about 90% (by weight of the composition), more preferably from about 10% (by weight of the composition) to about 80% (by weight of the composition), and more preferably from about 10% (by weight of the composition) to about 60% (by weight of the composition). Compositions comprising about 12.5% (by weight of the composition) mineral oil and about 37.5% (by weight of the composition) butyl lactate, or about 25% (by weight of the composition) mineral oil and about 25% (by weight of the composition) butyl lactate, or about 37.5% (by weight of the composition) mineral oil and about 12.5% (by weight of the composition) butyl lactate have been found to be particularly effective at killing insects such as cockroaches.

Isopropyl myristate may be present in the composition in an amount of from about 5% (by weight of the composition) to about 95% (by weight of the composition), more preferably from about 10% (by weight of the composition) to about 80% (by weight of the composition), and more preferably from about 10% (by weight of the composition) to about 60% (by weight of the composition). Compositions comprising about 60% (by weight of the composition) mineral oil and about 20% (by weight of the composition) isopropyl myristate, or about 50% (by weight of the composition) mineral oil and about 30% (by weight of the composition) isopropyl myristate, or about 40% (by weight of the composition) mineral oil and about 40% (by weight of the composition) isopropyl myristate have been found to be particularly effective at killing insects such as cockroaches.

Hexylene glycol may be present in the composition in an amount of from about 5% (by weight of the composition) to about 90% (by weight of the composition), and more preferably from about 10% (by weight of the composition) to about 60% (by weight of the composition). Compositions comprising about 60% (by weight of the composition) mineral oil and about 20% (by weight of the composition) hexylene glycol have been found to be particularly effective at killing insects such as cockroaches.

Dioxane may be present in the composition in an amount of from about 5% (by weight of the composition) to about 80% (by weight of the composition), more preferably from about 5% (by weight of the composition) to about 60% (by weight of the composition), and more preferably from about 10% (by weight of the composition) to about 60% (by weight of the composition). Compositions comprising about 40% (by weight of the composition) mineral oil and about 40% (by weight of the composition) dioxane have been found to be particularly effective at killing insects such as cockroaches.

D-limonene may be present in the composition in an amount of from about 3% (by weight of the composition) to about 90% (by weight of the composition), and more preferably from about 5% (by weight of the composition) to about 90% (by weight of the composition), and more preferably from about 5% (by weight of the composition) to about 60% (by weight of the composition). Compositions comprising about 40% (by weight of the composition) mineral oil and about 40% (by weight of the composition) d-limonene have been found to be particularly effective at killing insects such as cockroaches.

In one embodiment, the second active ingredient is an ester compound. When ester compounds are present in the pesticidal composition as a second active ingredient, additional second active ingredients that are not ester compounds may also be present in the composition. The amount of ester compounds that are present in the pesticidal composition may be at least about 50% of all the second active ingredients, at least about 65% of all the second active ingredients, at least about 75% of all the second active ingredients, at least about 85% of all the second active ingredients, at least about 95% of all the second active ingredients, or even at least about 99% of all the second active ingredients. In one embodiment, the total amount (i.e., about 100%) of second active ingredients present in the pesticidal composition is ester compounds.

The ester compounds present in the pesticidal composition may be selected from the group consisting of ethyl lactate, butyl lactate, isopropyl myristate, γ-butyrolactone, triacetin and combinations thereof. These listed esters may be present in the pesticidal composition in an amount of at least about 1% by weight of the composition, at least about 3%, at least about 5%, at least about 10% or even at least about 15% by weight of the composition. In one embodiment, the ester compounds are present in an amount from about 10% to about 60% by weight of the composition.

In another embodiment, the ester compounds are selected from the group consisting of ethyl lactate, butyl lactate, isopropyl myristate and combinations thereof. In yet another embodiment, the ester compounds are selected from the group consisting of ethyl lactate, γ-butyrolactone, triacetin and combinations thereof. In yet another aspect, the ester compounds are selected from the group consisting of ethyl lactate, γ-butyrolactone, triacetin and combinations thereof.

In one embodiment, the second active ingredient is an alcohol. The pesticidal composition may include one alcohol compound or more than one alcohol compound without departing from the scope of the present disclosure. When alcohols are present in the pesticidal composition as a second active ingredient, additional second active ingredients that are not alcohols may also be present in the composition. The amount of alcohol present in the pesticidal composition may be at least about 50% of all the second active ingredients, at least about 65% of all the second active ingredients, at least about 75% of all the second active ingredients, at least about 85% of all the second active ingredients, at least about 95% of all the second active ingredients, or even at least about 99% of all the second active ingredients. In one embodiment, the total amount (i.e., about 100%) of second active ingredients present in the pesticidal composition is an alcohol or alcohols.

The alcohol utilized in the second active ingredient may be selected from the group consisting of C1-C14 saturated straight-chain alcohols, isopropyl alcohol, 2-butanol, isobutyl alcohol, tertiary butyl alcohol, 2-butoxyethanol, 2-phenylethanol, diacetone alcohol, 2-ethoxyethanol and combinations thereof. These alcohols may be present in the pesticidal composition in at least about 1%, at least about 3%, at least about 5%, at least about 10% or even at least about 15% by weight of the composition. In one embodiment, the alcohols are present in an amount from about 10% to about 60% by weight of the composition.

In one embodiment, the alcohol is selected from the group consisting of methanol, 1-proponal, 1-butanol, 1-hexanol, 1-heptanol, 1-octanol, 1-nonanol, 1-decanol, 1-undecanol, 1-dodecanol, 1-tetradecanol, 2-butanol, isobutyl alcohol, tertiary butyl alcohol, 2-butoxyethanol, 2-phenylethanol, diacetone alcohol, 2-ethoxyethanol and combinations thereof. In a further embodiment, the alcohol is selected from methanol, 1-proponal, 1-butanol, 1-hexanol, 1-heptanol, 1-octanol, 1-nonanol, 1-decanol, 1-undecanol, 1-dodecanol, 1-tetradecanol, 2-butanol, isobutyl alcohol, tertiary butyl alcohol, 2-butoxyethanol, 2-phenylethanol, diacetone alcohol and combinations thereof. The alcohol may also be selected from the group consisting of 2-butanol, isobutyl alcohol, tertiary butyl alcohol, 2-butoxyethanol, 2-phenylethanol, diacetone alcohol, 2-ethoxyethanol and combinations thereof.

In another embodiment, the alcohol is selected from the group consisting of C1-C14 saturated straight-chain alcohols, isopropyl alcohol, 2-butanol, isobutyl alcohol, tertiary butyl alcohol, 2-butoxyethanol, 2-phenylethanol, diacetone alcohol, 2-ethoxyethanol and combinations thereof.

The pesticidal composition may include a plurality of alcohol compounds including a plurality of C1-C 14 saturated straight chain alcohols. In one embodiment, the C1-C14 saturated straight-chain alcohol is selected from the group consisting of methanol, ethanol, 1-proponal, 1-butanol, 1-hexanol, 1-heptanol, 1-octanol, 1-nonanol, 1-decanol, 1-undecanol, 1-dodecanol, 1-tetradecanol and combinations thereof.

In another embodiment, the alcohol is a C1-C9 saturated straight-chain alcohol and, in another embodiment, is a C1-C6 straight chain alcohol. In one embodiment, the alcohol is a C3-C7 saturated straight-chain alcohol.

In a particular embodiment, mineral oil and a second active ingredient selected from the group consisting of C1-C14 saturated straight-chain alcohol, isopropyl alcohol, 2-butanol, isobutyl alcohol, tertiary butyl alcohol, 2-butoxyethanol, 2-phenylethanol or diacetone alcohol may be present in the composition in a ratio based on the $LD_{10}$ or $LD_{50}$ value of the alcohol, which optimizes the biological effect of the blend.

For example, where the second active ingredient is isopropyl alcohol, 2-butanol, isobutyl alcohol, tertiary butyl alcohol, 2-butoxyethanol, 2-phenylethanol, diacetone alcohol, or a C1-C14 saturated straight chain alcohol, the $LD_{10}$ of each of the active ingredients is determined, for instance, by the methods described in Example 9. A ratio is then determined based on about half of the $LD_{10}$ for mineral oil and about the $LD_{10}$ of the second active ingredient. For example, as detailed in Example 9, the $LD_{10}$ for PD23 mineral oil was determined to be 0.754 mg/insect and the $LD_{10}$ for diacetone alcohol was determined to be 0.255 mg/insect. About half of the $LD_{10}$ of PD23 is about 0.4 mg, while about the $LD_{10}$ of diacetone alcohol is about 0.3 mg. Accordingly, for a composition comprising PD23 and diacetone alcohol, a ratio corresponding to the above amounts is 4 parts PD23 to 3 parts diacetone alcohol, or 4:3. Thus, a composition of this particular embodiment may comprise PD23 and diacetone alcohol, among other things, in a ratio of 4:3.

Similarly, for example, in a composition comprising PD23 and 1-propanol, those active ingredients may be present in the composition in a ratio of about 4:4.5 or about 1:1. The ratio is determined based on the $LD_{10}$ for 1-propanol and PD23, respectively, of 0.472 mg/insect and 0.754 mg/insect. About half the $LD_{10}$ of PD23 is about 0.4 mg, and the $LD_{10}$ of 1-propanol is about 0.45 mg, giving a ratio of about 4:4.5, or about 1:1.

Alternatively, the ratio may be determined as above, but based on the $LD_{10}:LD_{10}$ of the mineral oil and second active ingredient. So, for example, in a composition comprising PD23 and 1-propanol, the PD23 and 1-propanol are present in a ratio of 8:4.5, or about 2:1.

Similarly, a C1-C14 saturated straight-chain alcohol, isopropyl alcohol, 2-butanol, isobutyl alcohol, tertiary butyl alcohol, 2-butoxyethanol, 2-phenylethanol or diacetone alcohol may be present in the composition in a ratio relative to the mineral oil in the composition, where this ratio is determined based on the $LD_{50}$ for the alcohol and the $LD_{50}$ of the mineral oil. As above with respect to ratios based on $LD_{10}$, such ratios may be determined based on $LD_{50}:LD_{50}$; or may alternatively be determined based on 0.5 $LD_{50}$ for mineral oil and $LD_{50}$ for the second active ingredient.

In another embodiment, mineral oil and a second active ingredient selected from the group consisting of C1-C14 saturated straight-chain alcohol, isopropyl alcohol, 2-butanol, isobutyl alcohol, tertiary butyl alcohol, 2-butoxyethanol, 2-phenylethanol, diacetone alcohol, 2-ethoxyethanol or combinations thereof may be present in the composition in a ratio which may be determined based on the $LD_{10}$ or $LD_{50}$.

In one embodiment, the second active ingredient is a compound selected from the group consisting of hexylene glycol, dioxane, d-limonene, nitromethane, acetophenone, pyridine and combinations thereof. These listed compounds may be included with other second active ingredients. The amount of the listed compounds in the pesticidal composition may be at least about 50% of all the second active ingredients, at least about 65% of all the second active ingredients, at least about 75% of all the second active ingredients, at least about 85% of all the second active ingredients, at least about 95% of all the second active ingredients, or even at least about 99% of all the second active ingredients. In one embodiment, the total amount (i.e., about 100%) of second active ingredients present in the pesticidal composition is compounds selected from hexylene glycol, dioxane, d-limonene, nitromethane, acetophenone, pyridine and combinations thereof.

In another embodiment, the second active ingredient is selected from the group consisting of hexylene glycol, dioxane, d-limonene, nitromethane, acetophenone, pyridine and combinations thereof.

In another embodiment, the second active ingredient is selected from hexylene glycol, dioxane, d-limonene and combinations thereof. In a further embodiment, the second active ingredient is selected from nitromethane, acetophenone, pyridine and combinations thereof.

These compounds may be present in the pesticidal composition in at least about 1%, at least about 3%, at least about 5%, at least about 10% or even at least about 15% by weight of the composition. In one embodiment, the listed compounds are present in an amount from about 10% to about 60% by weight of the composition.

In certain embodiments, the pesticidal compositions may comprise mineral oil plus two or more of the second active ingredients. For instance, in one particular embodiment, the pesticidal composition comprises mineral oil, ethyl lactate, and isopropyl myristate. In this embodiment, the pesticidal composition preferably comprises from about 5% (by weight of the composition) to about 30% (by weight of the composition) of ethyl lactate, and more typically from about 5% (by weight of the composition) to about 15% (by weight of the composition) of ethyl lactate; from about 5% (by weight of the composition) to about 60% (by weight of the composition) of isopropyl myristate, and more typically from about 5% (by weight of the composition) to about 30% (by weight of the composition) of isopropyl myristate; and from about 20% (by weight of the composition) to about 70% (by weight of the composition) of mineral oil.

In another particular embodiment, the pesticidal composition comprises mineral oil, d-limonene, and ethyl lactate. In this embodiment, the pesticidal composition preferably comprises from about 5% (by weight of the composition) to about 60% (by weight of the composition) of d-limonene, from about 5% (by weight of the composition) to about 30% (by weight of the composition) of ethyl lactate, and from about 20% (by weight of the composition) to about 90% (by weight of the composition) of mineral oil.

In yet another particular embodiment, the pesticidal composition comprises mineral oil, d-limonene, and butyl lactate. In this embodiment, the pesticidal composition preferably comprises from about 5% (by weight of the composition) to about 20% (by weight of the composition) of d-limonene, from about 5% (by weight of the composition) to about 20% (by weight of the composition) of butyl lactate, and from about 30% (by weight of the composition) to about 80% (by weight of the composition) of mineral oil.

In still another particular embodiment, the pesticidal composition may comprise mineral oil, d-limonene, ethyl lactate, and isopropyl myristate. In this embodiment, the pesticidal composition preferably comprises from about 5% (by weight of the composition) to about 20% (by weight of the composition) of d-limonene, from about 5% (by weight of the composition) to about 20% (by weight of the composition) of ethyl lactate, from about 20% (by weight of the composition) to about 40% (by weight of the composition) of isopropyl myristate, and from about 30% (by weight of the composition) to about 80% (by weight of the composition) of mineral oil.

In addition to the first and one or more second active ingredients, the pesticidal compositions of the present disclosure may further comprise a plant essential oil or derivative thereof, which may also have pesticidal properties. Such plant essential oils or derivatives may be extracted from natural sources or synthetically made, and generally contain, as at least one major constituent, an acyclic monoterpene alcohol or aldehyde, a benzenoid aromatic compound containing at least one oxygenated substituent or side chain, or a monocarbocyclic terpene generally having a six membered ring bearing one or more oxygenated substituents. Examples of such essential oils or their derivatives include, but are not limited to, members selected from the group consisting of aldehyde C16 (pure), alpha-terpineol, amyl cinnamic aldehyde, amyl salicylate, anisic aldehyde, benzyl alcohol, benzyl acetate, cinnamaldehyde, cinnamic alcohol, carvacrol, carveol, citral, citronellal, citronellol, dimethyl salicylate, eucalyptol (cineole), eugenol, iso-eugenol, galaxolide, geraniol, guaiacol, ionone, menthol, methyl anthranilate, methyl ionone, methyl salicylate, nerol, alpha-phellandrene, pennyroyal oil, perillaldehyde, 1- or 2-phenyl ethyl alcohol, 1- or 2-phenyl ethyl propionate, piperonal, piperonyl acetate, piperonyl alcohol, D-pulegone, terpinen-4-ol, terpinyl acetate, 4-tert butylcyclohexyl acetate, thyme oil (white and red), thymol, trans-anethole, vanillin, ethyl vanillin, and the like.

Other suitable oils include, for example, castor oil, cedar oil, cinnamon and cinnamon oil, citronella and citronella oil, cloves and clove oil, corn oil, cottonseed oil, garlic and garlic oil, geranium oil, lemongrass oil, linseed oil, mint and mint oil, peppermint and peppermint oil, rosemary and rosemary oil, sesame and sesame oil, soybean oil, white pepper, and the like. Preferably, the plant essential oil or derivative is geraniol.

The pesticidal compositions will typically comprise from about 1% (by weight of the composition) to about 60% (by weight of the composition of the plant essential oil or derivative, more typically from about 2% (by weight of the composition) to about 60% (by weight of the composition), and more typically from about 2% (by weight of the composition) to about 20% (by weight of the composition) of the plant essential oil or derivative.

In one embodiment, the pesticidal composition includes a first active ingredient that is a mineral oil, at least one second active ingredient that is selected from the group consisting of ethyl lactate, butyl lactate, isopropyl myristate, hexylene glycol, dioxane, d-limonene, a C1-C14 saturated straight-chain alcohol, isopropyl alcohol, 2-butanol, isobutyl alcohol, tertiary butyl alcohol, 2-butoxyethanol, 2-phenylethanol, diacetone alcohol, and combinations thereof and a third active ingredient that is a plant essential oil or derivative. In one embodiment, the plant essential oil or derivative is geraniol. In another embodiment, the composition also includes nerol.

In one embodiment, the composition comprises from about 10% to about 70% of the first ingredient by weight of the composition, from about 5% to about 50% of the second ingredient by weight of the composition and from about 0.5% to about 15% of the third active ingredient by weight of the composition.

The amount of geraniol present in the composition may be at least about 2% by weight of the composition, at least about 4% or at least about 6% by weight of the composition. In one embodiment, the amount of geraniol present in the composition is from about 0.5% to about 8% by weight of the composition. Nerol may be present in the composition in an amount from about 0.5% to about 3% by weight of the composition.

In another embodiment, the pesticidal composition comprises mineral oil, and at least two second active ingredients, each second active ingredient being selected from the group consisting of ethyl lactate, butyl lactate, isopropyl myristate, hexylene glycol, dioxane, d-limonene, a C1-C14 saturated straight-chain alcohol, isopropyl alcohol, 2-butanol, isobutyl alcohol, tertiary butyl alcohol, 2-butoxyethanol, 2-phenylethanol, diacetone alcohol, and combinations thereof and a third active ingredient that is a plant essential oil or derivative. In one embodiment, the plant essential oil or derivative is geraniol. In another embodiment, the composition also includes nerol.

In another embodiment, the pesticidal composition comprises a mineral oil, ethyl lactate, isopropyl myristate and geraniol. The composition may also include nerol. Additional additives may include essential oils such as lemongrass oil and carbon dioxide (described below).

In one embodiment, the pesticidal composition comprises, by weight of the composition, about 43% mineral oil, about 15% ethyl lactate, about 30% isopropyl myristate and about 6% geraniol. The composition may also include about 3% nerol and about 1% lemongrass oil.

Additionally, the pesticidal composition may further comprise other known insecticidal or pesticidal agents, including, for example, synergists such as piperonyl butoxide, MGK 264, and dillapiol; as well as other plant-derived insecticidal or pesticidal materials such as pyrethrum.

The composition may also comprise an amount of water. In various embodiments, the composition contains water in an amount of, by weight of the composition, at least about 10%, at least about 25%, at least about 50% or even at least about 75%. In one embodiment, the amount of water in the solution is from about 10% to about 50% by weight of the composition and, in another embodiment, from about 25% to about 75% by weight of the composition.

The compositions of the present disclosure may further comprise a suitable solvent, carrier or emulsifier. Examples of suitable solvents or carriers include water, acetone, alcohols such as ethanol and isopropyl alcohol, dimethyl ether, and chlorinated hydrocarbon solvents such as methylene chloride and methyl chloroform. Examples of emulsifiers would include soaps (such as fatty acid soaps), cationic, ionic and non-ionic compounds. Additional carriers for use in various granular formulations include, for example, corn cob grits, diatomaceous earth, sand, clay, and the like.

The pesticidal compositions of the present disclosure may be dispensed in any conventional manner, e.g., from a standard pump-spray container. In one embodiment, the pesticide is in a ready-to-use form in which the composition does not need to be diluted before application. Alternatively, the pesticidal composition may be in a concentrate form. The end-user of the concentrate composition may dilute the concentrate prior to use by, for example, addition of water. In one embodiment, the pesticidal composition is diluted in the pump spray bottle. In various embodiments, the concentrate pesticidal composition may be diluted by addition of water in an amount of, by weight of the concentrate composition, at least about 40%, at least about 50%, at least about 75%, at least about 100%, at least about 150%, at least about 200% or even at least about 300%.

When the pesticidal composition is present in a concentrate form, in some embodiments, dilution may cause formation of a water-concentrate emulsion. The pesticidal concentrate may include emulsifiers such as surfactants (e.g., surfactants such as fatty acid soaps). Suitable compounds may be cationic, ionic, and non-ionic. Suitable emulsifying compounds include alkyl aryl sulionate-based emulsifiers, polyoxyethylenes and long-chain alcohols.

In one embodiment, the pesticidal composition is packaged in a pressurized container such as a conventional aerosol container or the like. The composition may be pressurized utilizing any suitable propellant. Examples of suitable propellants include expandable gases such as carbon dioxide, nitrogen, propane, n-butane, isobutane, blends of propane and butane, HFC-152a (difluoroethane), HFC-134a (1,1,1,2-tetrafluoroethane), and combinations thereof.

Any conventional technique may be used to charge the aerosol container with carbon dioxide or other expandable gas. In one embodiment, the gasser-shaker method may be used. This method involves shaking or agitating the container and its contents as the carbon dioxide (or other gas) is forced into the container through a valve, with the rest of the composition having been introduced into the container prior to installation of the valve. The rate of injection of the gas depends on the valve orifice size, and the shaking time depends on the container size, the amount of liquid, and the degree of agitation, as well as the temperature.

Alternatively, the pesticidal composition may be saturated with carbon dioxide prior to introduction into the container, and then pumped under pressure to a rotary undercap filler and filled as in a normal undercap operation, or pressured into containers already equipped with valves. Other suitable methods known in the art may also be used.

Other examples of suitable propellants which may be used are known in the art and include, for example, dimethyl ether, methyl ethyl ether, nitrous oxide, and the like.

Typically the composition will comprise propellant in an amount of from about 2% (by weight of the composition) to about 90% (by weight of the composition), and more typically in an amount of from about 2% (by weight of the composition) to about 10% (by weight of the composition).

As noted above, the pesticidal compositions of the present disclosure may be sprayed or otherwise contacted with insects or other pests to effectively control insect or other pest populations. Thus, in one embodiment, the present disclosure is directed to a method of controlling insects and pests. The method comprises contacting the insects and pests with a pesticidally effective amount of a composition of the present disclosure.

In one embodiment, an arthropod is contacted with the pesticidal composition in a pesticidally effective amount. For purposes of the present disclosure, a "pesticidally effective amount" of the composition includes amounts that repel the arthropod or other pest and may include, in another embodiment, amounts of the composition that kill the arthropod or other pest.

The pesticidal compositions of embodiments of the present disclosure may be used to control arthropods and, in another embodiment, to control insects. In one embodiment, the pesticidal composition is used to control cockroaches. Control of the pest (e.g., arthropod, insect, cockroach, etc.) may include contacting the pest with the pesticidal composition. In one embodiment, the pest is contacted with the pesticidal composition by spraying the composition directly on the crawling arthropod, flying insect or other pest. The composition may be sprayed in a sufficient amount to cause death. The pesticidal composition may also be sprayed in locations at which the pest is likely to come into contact with the composition.

The amount of the pesticidal composition required to kill insects or other pests and the time until pest death will vary depending on the composition components, the type of insect species and its life stage, and the like. The time required to kill a pest contacted with the pesticidal composition of the present disclosure will typically range from mere seconds to several hours.

The pesticidal compositions of the present disclosure are particularly effective against cockroaches, including the species *Periplaneta Americana* (American cockroach), *Blattella germanica* (German cockroach), *Blattella asahinai* (Asian cockroach), and *Blatta orientalis* (Oriental cockroach). However, the pesticidal compositions may also be used against a wide variety of other crawling insects or other arthropods, such as ants, water bugs, silverfish, crickets, spiders, ticks, mites, sowbugs, pillbugs, beetles, earwigs, centipedes, and the like. As used herein, the term "water bugs" refers to aquatic insects in the order *Hemiptera*. Examples of water bugs include giant water bugs, creeping water bugs, water scorpions, water boatmen, backswimmers, and the like. In one embodiment, the pesticidal compositions are effective against various flying insects including flies, mosquitoes, gnats, moths, wasps, hornets, bees, and the like.

The pesticidal compositions of the present disclosure generally result in at least 80% mortality, more preferably at least 95% mortality, and more preferably 100% mortality of the insects on contact, depending on the specific composition, the amount of composition applied to the insect and the insect species and life stage.

Having described the disclosure in detail, it will be apparent that modifications and variations are possible without departing from the scope of the disclosure defined in the appended claims.

EXAMPLES

The following non-limiting examples are provided to further illustrate the present disclosure.

Unless otherwise indicated, the mineral oil used in the following examples was PD-23 (available from Chemtura Corporation, Middlebury, Conn.), which is a light grade petroleum distillate having a flash point of 230° F. (110° C.), as measured by ASTM D-92, and a vapor pressure of less than 0.1 mmHg at 20° C. PD-23 is a highly refined petroleum distillate that resembles a very clear oil, and is made by fractionating oil to a narrow boiling range, then catalytically hydrotreating it to remove all aromatic and other unsaturated hydrocarbons. PD-23 is hydrophobic, colorless, tasteless, virtually odorless, and color fast.

Example 1

In this example, the effectiveness of compositions comprising various concentrations of mineral oil and/or ethyl lactate at killing German cockroaches was tested.

To begin, compositions comprising mineral oil and/or ethyl lactate in the following concentrations were prepared: 100% (wt/wt) mineral oil/0% (wt/wt) ethyl lactate; 90% (wt/wt) mineral oil/10% (wt/wt) ethyl lactate; 75% (wt/wt) mineral oil/25% (wt/wt) ethyl lactate; 50% (wt/wt) mineral oil/50% (wt/wt) ethyl lactate; 25% (wt/wt) mineral oil/75% (wt/wt) ethyl lactate; 10% (wt/wt) mineral oil/90% (wt/wt) ethyl lactate; 0% (wt/wt) mineral oil/100% (wt/wt) ethyl lactate. The ethyl lactate was obtained from Vertech Biosolvents, Inc., Downers Grove, Ill.

Prior to testing, each composition containing either mineral oil, ethyl lactate, or a combination of mineral oil and ethyl lactate was diluted by 50% by mixing the composition with acetone in a 1:1 ratio (wt/wt) to reduce viscosity prior to application of the compositions to the cockroaches. The amount of mineral oil, ethyl lactate, and acetone present in the final composition (A-G) is set forth below in Table 1.

Toxicity evaluations were performed on 7-14 day old adult male and female German cockroaches (SCJ Strain, S.C. Johnson & Son, Racine, Wis.). Approximately 12 cockroaches were transferred to individual 100×20 mm polystyrene Petri dishes and anesthetized with a 15-25 second exposure to carbon dioxide. The inside edge of each Petri dish was lightly coated with mineral oil plus petroleum jelly in a 1:3 (wt/wt) ratio to minimize escape. Anesthetized cockroaches were positioned with their ventral side up, and a 1 µl drop of the diluted test composition was applied to the area between the meso- and metathoracic legs using a Rainin L-10, 10 µl capacity pipette (Rainin Instrument, LLC, Oakland, Calif.). Five replications of 12 male cockroaches were done for each test composition. Separate tests were done using female cockroaches. Results were evaluated at 24 hours following treatment. Cockroaches were scored as either alive (dorsal side up, active movement when abdomen prodded with dissecting probe) or moribund/dead (dorsal side up and no movement when abdomen prodded or ventral side up and insect unable to right itself).

Results are shown in FIG. 1 and Table 1, which lists the number of dead cockroaches out of 60 total cockroaches for each test performed using the diluted test compositions (A-G).

TABLE 1

| Composition | Mineral oil (wt/wt) | Ethyl lactate (wt/wt) | Acetone (wt/wt) | Males (# dead out of 60) | Females (# dead out of 60) |
|---|---|---|---|---|---|
| A | 50% | 0% | 50% | 6 | 1 |
| B | 45% | 5% | 50% | 7 | 0 |
| C | 37.5% | 12.5% | 50% | 40 | 20 |
| D | 25% | 25% | 50% | 56 | 44 |
| E | 12.5% | 37.5% | 50% | 57 | 40 |
| F | 5% | 45% | 50% | 49 | 38 |
| G | 0% | 50% | 50% | 3 | 0 |

As can be seen from these results, cockroaches treated with test composition C-F (containing both mineral oil and ethyl lactate) had significantly higher mortality rates than cockroaches treated with only mineral oil (composition A) or only ethyl lactate (composition G), indicating a synergistic effect when the combination of mineral oil and ethyl lactate is used.

Example 2

In this example, the effectiveness of compositions comprising various concentrations of mineral oil and/or butyl lactate at killing cockroaches was tested.

To begin, compositions comprising mineral oil and/or butyl lactate in the following concentrations were prepared: 100% (wt/wt) mineral oil/0% (wt/wt) butyl lactate; 90% (wt/wt) mineral oil/10% (wt/wt) butyl lactate; 75% (wt/wt) mineral oil/25% (wt/wt) butyl lactate; 50% (wt/wt) mineral oil/50% (wt/wt) butyl lactate; 25% (wt/wt) mineral oil/75% (wt/wt) butyl lactate; 10% (wt/wt) mineral oil/90% (wt/wt) butyl lactate; 0% (wt/wt) mineral oil/100% (wt/wt) butyl lactate. The butyl lactate was obtained from Vertech Biosolvents, Inc., Downers Grove, Ill.

Prior to testing, each composition containing either mineral oil, butyl lactate, or a combination of mineral oil and butyl lactate was diluted by 50% by mixing the composition with acetone in a 1:1 ratio (wt/wt) to reduce viscosity prior to application of the composition to the cockroaches. The amount of mineral oil, butyl lactate, and acetone present in the final compositions (H-N) is set forth below in Table 2.

Figure 2:
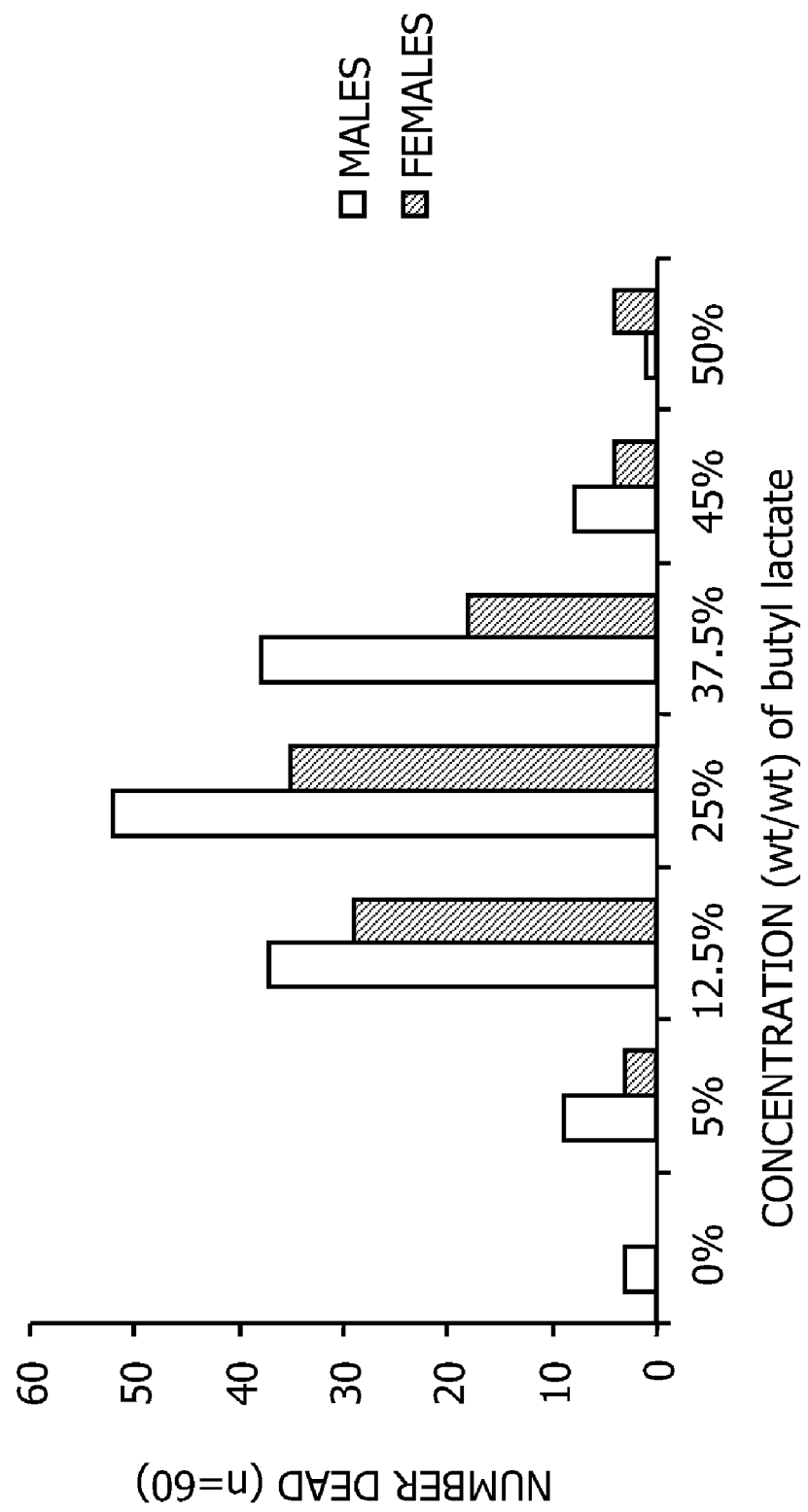
FIG. 2 is a chart depicting the effects of compositions comprising mineral oil and/or butyl lactate on the mortality of adult German cockroaches as discussed in Example 2.

Tests were performed as described in Example 1. The results are shown in FIG. 2 and Table 2 below.

TABLE 2

| Composition | Mineral oil (wt/wt) | Butyl lactate (wt/wt) | Acetone (wt/wt) | Males (# dead out of 60) | Females (# dead out of 60) |
|---|---|---|---|---|---|
| H | 50% | 0% | 50% | 3 | 0 |
| I | 45% | 5% | 50% | 9 | 3 |
| J | 37.5% | 12.5% | 50% | 37 | 29 |
| K | 25% | 25% | 50% | 52 | 35 |
| L | 12.5% | 37.5% | 50% | 38 | 18 |
| M | 5% | 45% | 50% | 8 | 4 |
| N | 0% | 50% | 50% | 1 | 4 |

As can be seen from these results, cockroaches treated with test composition J-L (containing both mineral oil and butyl lactate) had significantly higher mortality rates than cockroaches treated with only mineral oil (composition H) or only butyl lactate (composition N), indicating a synergistic effect when the combination of mineral oil and butyl lactate is used.

Example 3

In this example, the effectiveness of compositions comprising various concentrations of mineral oil and/or hexylene glycol at killing cockroaches was tested.

To begin, compositions comprising mineral oil, hexylene glycol, or a combination of mineral oil and hexylene glycol were prepared. The amount of mineral oil and/or hexylene glycol in each composition is set forth below in Table 3, with the remainder of each composition consisting of acetone.

Tests were generally performed as described in Example 1, except the number of cockroaches (all male) tested for each composition is set forth below in Table 3, and the compositions were not further diluted with acetone in a 1:1 (wt/wt) ratio prior to testing. The results are shown in Table 3 below, which lists the number of cockroaches tested for each composition, the number of dead cockroaches out of the total number of cockroaches tested, the square root percent dead cockroaches, the proportion of dead cockroaches, and the arcsine square root percent dead cockroaches.

TABLE 3

| Composition (% wt/wt) | # tested | # dead | Square root % dead | Proportion dead | Arcsine square root % dead |
|---|---|---|---|---|---|
| Hexylene glycol (20%) | 14 | 1 | 0.2672612 | 0.07142857 | 0 |
| Hexylene glycol (20%) | 12 | 0 | 0 | 0 | 0 |
| Hexylene glycol (20%) | 13 | 3 | 0.4803845 | 0.23076923 | 28.7105148 |
| Hexylene glycol (20%) | 14 | 0 | 0 | 0 | 0 |
| Mineral oil (80%) | 14 | 2 | 0.3779645 | 0.14285714 | 22.2076543 |
| Mineral oil (80%) | 14 | 1 | 0.2672612 | 0.07142857 | 15.50135957 |
| Mineral oil (80%) | 13 | 2 | 0.3922323 | 0.15384615 | 23.09346927 |
| Mineral oil (80%) | 14 | 1 | 0.2672612 | 0.07142857 | 15.50135957 |
| Mineral oil (60%), hexylene glycol (20%) | 13 | 11 | 0.9198662 | 0.84615385 | 66.90653073 |

TABLE 3-continued

| Composition (% wt/wt) | # tested | # dead | Square root % dead | Proportion dead | Arcsine square root % dead |
|---|---|---|---|---|---|
| Mineral oil (60%), hexylene glycol (20%) | 14 | 11 | 0.8864053 | 0.78571429 | 62.42495229 |
| Mineral oil (60%), hexylene glycol (20%) | 14 | 13 | 0.9636241 | 0.92857143 | 74.49864043 |

As can be seen from these results, cockroaches treated with compositions containing both mineral oil and hexylene glycol had significantly higher mortality rates than cockroaches treated with only mineral oil or only hexylene glycol, indicating a synergistic effect when the combination of mineral oil and hexylene glycol is used.

Example 4

In this example, the effectiveness of compositions comprising various concentrations of mineral oil and/or isopropyl myristate at killing cockroaches was tested.

To begin, compositions comprising mineral oil, isopropyl myristate, or a combination of mineral oil and isopropyl myristate were prepared. The amount of mineral oil and/or isopropyl myristate in each composition is set forth below in Table 4, with the remainder of each composition consisting of acetone.

Tests were generally performed as described in Example 1, except the number of cockroaches (all male) tested for each composition is set forth below in Table 4, and the compositions were not further diluted with acetone in a 1:1 (wt/wt) ratio prior to testing. The results are shown in Table 4 below, which lists the number of cockroaches tested for each composition, the number of dead cockroaches out of the total number of cockroaches tested, the square root percent dead cockroaches, the proportion of dead cockroaches, and the arcsine square root percent dead cockroaches.

TABLE 4

| Composition (% wt/wt) | # tested | # dead | Square root % dead | Proportion dead | Arcsine square root % dead |
|---|---|---|---|---|---|
| Isopropyl myristate (80%) | 15 | 1 | 0.2582 | 0.06667 | 14.9632174 |
| Isopropyl myristate (80%) | 17 | 0 | 0 | 0 | 0 |
| Isopropyl myristate (80%) | 15 | 1 | 0.2582 | 0.06667 | 14.9632174 |
| Isopropyl myristate (80%) | 12 | 1 | 0.28868 | 0.08333 | 16.7786549 |
| Mineral oil (80%) | 15 | 2 | 0.36515 | 0.13333 | 21.416714 |
| Mineral oil (80%) | 17 | 1 | 0.24254 | 0.05882 | 14.0362435 |
| Mineral oil (80%) | 15 | 2 | 0.36515 | 0.13333 | 21.416714 |
| Mineral oil (80%) | 12 | 0 | 0 | 0 | 0 |
| Mineral oil (80%) | 15 | 2 | 0.36515 | 0.13333 | 21.416714 |
| Mineral oil (40%), isopropyl myristate (40%) | 15 | 6 | 0.63246 | 0.4 | 39.2315205 |
| Mineral oil (40%), isopropyl myristate (40%) | 16 | 3 | 0.43301 | 0.1875 | 25.6589063 |
| Mineral oil (40%), isopropyl myristate (40%) | 15 | 4 | 0.5164 | 0.26667 | 31.0909304 |
| Mineral oil (40%), isopropyl myristate (40%) | 12 | 2 | 0.40825 | 0.16667 | 24.0948425 |
| Mineral oil (50%), isopropyl myristate (30%) | 15 | 8 | 0.7303 | 0.53333 | 46.9112769 |
| Mineral oil (50%), isopropyl myristate (30%) | 16 | 6 | 0.61237 | 0.375 | 37.7612439 |
| Mineral oil (50%), isopropyl myristate (30%) | 15 | 3 | 0.44721 | 0.2 | 26.5650512 |
| Mineral oil (50%), isopropyl myristate (30%) | 12 | 4 | 0.57735 | 0.33333 | 35.2643897 |
| Mineral oil (60%), isopropyl myristate (20%) | 15 | 4 | 0.5164 | 0.26667 | 31.0909304 |
| Mineral oil (60%), isopropyl myristate (20%) | 15 | 7 | 0.68313 | 0.46667 | 43.0887231 |
| Mineral oil (60%), isopropyl myristate (20%) | 15 | 4 | 0.5164 | 0.26667 | 31.0909304 |
| Mineral oil (60%), isopropyl myristate (20%) | 12 | 3 | 0.5 | 0.25 | 30 |

The combined data for each treatment group is set forth in Table 5 below.

TABLE 5

| Composition (% wt/wt) | Number of compositions | Average arcsine sq. root % dead | Variance |
|---|---|---|---|
| Isopropyl myristate (80%) | 4 | 11.67627243 | 61.3258864 |
| Mineral oil (80%) | 5 | 15.6572771 | 86.82285408 |
| Mineral oil (40%), isopropyl myristate (40%) | 4 | 30.01904993 | 46.70854263 |
| Mineral oil (50%), isopropyl myristate (30%) | 4 | 36.62549043 | 70.05079065 |
| Mineral oil (60%), isopropyl myristate (20%) | 4 | 33.81764598 | 38.46574917 |

As can be seen from these results, cockroaches treated with compositions containing both mineral oil and isopropyl myristate at all tested concentrations had significantly higher mortality rates than cockroaches treated with only mineral oil or only isopropyl myristate, indicating a synergistic effect when the combination of mineral oil and isopropyl myristate is used.

Example 5

In this example, the effectiveness of compositions comprising various concentrations of mineral oil and/or dioxane at killing cockroaches was tested.

To begin, compositions comprising mineral oil, dioxane, or a combination of mineral oil and dioxane were prepared. The amount of mineral oil and/or dioxane in each composition is set forth below in Table 6, with the remainder of each composition consisting of acetone.

Tests were generally performed as described in Example 1, except the number of cockroaches (all male) tested for each composition is set forth below in Table 6, and the compositions were not further diluted with acetone in a 1:1 (wt/wt) ratio prior to testing. The results are shown in Table 6, which lists the number of cockroaches tested for each composition, the number of dead cockroaches out of the total number of cockroaches tested, the square root percent dead cockroaches, the proportion of dead cockroaches, and the arcsine square root percent dead cockroaches.

TABLE 6

| Composition (% wt/wt) | # tested | # dead | Square root % dead | Proportion dead | Arcsine square root % dead |
|---|---|---|---|---|---|
| Dioxane (50%) | 10 | 0 | 0 | 0 | 0 |
| Dioxane (50%) | 14 | 0 | 0 | 0 | 0 |
| Dioxane (50%) | 14 | 0 | 0 | 0 | 0 |
| Dioxane (50%) | 12 | 0 | 0 | 0 | 0 |
| Dioxane (50%) | 13 | 1 | 0.277350098 | 0.07692308 | 16.10211375 |
| Mineral oil (80%) | 13 | 1 | 0.277350098 | 0.07692308 | 16.10211375 |
| Mineral oil (80%) | 14 | 2 | 0.377964473 | 0.14285714 | 22.2076543 |
| Mineral oil (80%) | 14 | 2 | 0.377964473 | 0.14285714 | 22.2076543 |
| Mineral oil (80%) | 14 | 1 | 0.267261242 | 0.07142857 | 15.50135957 |
| Mineral oil (80%) | 13 | 2 | 0.39223227 | 0.15384615 | 23.09346927 |
| Mineral oil (40%), dioxane (40%) | 14 | 10 | 0.845154255 | 0.71428571 | 57.68846676 |
| Mineral oil (40%), dioxane (40%) | 14 | 11 | 0.88640526 | 0.78571429 | 62.42495229 |
| Mineral oil (40%), dioxane (40%) | 14 | 11 | 0.88640526 | 0.78571429 | 62.42495229 |
| Mineral oil (40%), dioxane (40%) | 15 | 9 | 0.774596669 | 0.6 | 50.76847952 |
| Mineral oil (40%), dioxane (40%) | 13 | 12 | 0.960768923 | 0.92307692 | 73.89788625 |

As can be seen from these results, cockroaches treated with compositions containing both mineral oil and dioxane had significantly higher mortality rates than cockroaches treated with only mineral oil or only dioxane, indicating a synergistic effect when the combination of mineral oil and dioxane is used.

Example 6

In this example, the effectiveness of compositions comprising various concentrations of mineral oil and/or d-limonene at killing cockroaches was tested.

To begin, compositions comprising mineral oil, d-limonene, or a combination of mineral oil and d-limonene were prepared. The amount of mineral oil and/or d-limonene in each composition is set forth below in Table 7, with the remainder of each composition consisting of acetone.

Tests were generally performed as described in Example 1, except the number of cockroaches (all male) tested for each composition is set forth below in Table 7, and the compositions were not further diluted with acetone in a 1:1 (wt/wt) ratio prior to testing. The results are shown in Table 7, which lists the number of cockroaches tested for each composition, the number of dead cockroaches out of the total number of cockroaches tested, the square root percent dead cockroaches, the proportion of dead cockroaches, and the arcsine square root percent dead cockroaches.

TABLE 7

| Composition (% wt/wt) | # tested | # dead | Square root % dead | Proportion dead | Arcsine square root % dead |
|---|---|---|---|---|---|
| d-limonene (40%) | 14 | 1 | 0.267261242 | 0.0714286 | 15.50135957 |
| d-limonene (40%) | 12 | 0 | 0 | 0 | 0 |
| d-limonene (40%) | 15 | 2 | 0.365148372 | 0.1333333 | 21.41671403 |
| d-limonene (40%) | 14 | 2 | 0.377964473 | 0.1428571 | 22.2076543 |
| Mineral oil (80%) | 14 | 2 | 0.377964473 | 0.1428571 | 22.2076543 |
| Mineral oil (80%) | 14 | 1 | 0.267261242 | 0.0714286 | 15.50135957 |
| Mineral oil (80%) | 13 | 2 | 0.39223227 | 0.1538462 | 23.09346927 |
| Mineral oil (80%) | 14 | 1 | 0.267261242 | 0.0714286 | 15.50135957 |
| Mineral oil (40%), d-limonene (40%) | 14 | 6 | 0.654653671 | 0.4285714 | 40.89339465 |
| Mineral oil (40%), d-limonene (40%) | 13 | 5 | 0.620173673 | 0.3846154 | 38.3288181 |
| Mineral oil (40%), d-limonene (40%) | 14 | 12 | 0.9258201 | 0.8571429 | 67.7923457 |
| Mineral oil (40%), d-limonene (40%) | 14 | 7 | 0.707106781 | 0.5 | 45 |

The combined data for each treatment group is set forth in Table 8 below.

TABLE 8

| Composition (% wt/wt) | Number of compositions | Average arcsine sq. root % dead | Variance |
|---|---|---|---|
| d-limonene (40%) | 4 | 14.78145 | 106.0618 |
| Mineral oil (80%) | 4 | 19.076 | 17.16779 |
| Mineral oil (40%), d-limonene (40%) | 4 | 48.00363 | 181.5903 |

As can be seen from these results, cockroaches treated with compositions containing both mineral oil and d-limonene had significantly higher mortality rates than cockroaches treated with only mineral oil or only d-limonene, indicating a synergistic effect when the combination of mineral oil and d-limonene is used.

Example 7

In this example, the effectiveness of compositions comprising various types of mineral oil at killing cockroaches was tested.

To begin, compositions comprising one of three different types of mineral oil in varying concentrations were prepared. The mineral oils used in this example were PD-23 (Sample No. 88446, 1997, available from Chemtura Corporation, Middlebury, Conn.), which is a low viscosity (e.g., about 2.6 cSt at 40° C. or about 34 SUS at 100° F. (38° C.)) petroleum distillate; PD-25 (Sample No. 88447, available from Chemtura Corporation, Middlebury, Conn.), which is a medium viscosity (e.g., about 3.5 cSt at 40° C. or about 39 SUS at 100° F. (38° C.)) petroleum distillate; and PD-28 (Sample No. 88448, 1997, available from Chemtura Corporation, Middlebury, Conn.), which is a relatively high viscosity (e.g., about 4.2 cSt at 40° C. or about 39 SUS at 100° F. (38° C.)) petroleum distillate. The amount of each type of mineral oil in each composition is set forth below in Table 9, with the remainder of the composition comprising ethanol.

Tests were generally performed as described in Example 1, except 2 µl of the compositions were applied to each cockroach, the number of cockroaches (all male) tested for each diluted composition is set forth below in Table 9, and the compositions were not further diluted with acetone in a 1:1 (wt/wt) ratio prior to testing. The results are shown in Table 9.

TABLE 9

| Composition (% wt/wt) | # tested | # dead |
|---|---|---|
| PD-23 (50%) | 10 | 10 |
| PD-23 (20%) | 10 | 2 |
| PD-23 (20%) | 9 | 2 |
| PD-25 (50%) | 9 | 8 |
| PD-25 (20%) | 11 | 0 |
| PD-28 (50%) | 9 | 5 |
| PD-28 (20%) | 10 | 0 |

As can be seen from these results, compositions containing the higher concentration of mineral oil (i.e., the 50% compositions) were more effective against adult German cockroaches than the lower concentration compositions (i.e., the 20% compositions). Of the 20% compositions, only the PD-23 had any effect against the cockroaches. These results indicate that the lightest weight mineral oil used in these tests, PD-23, was the most active against adult German cockroaches.

Example 8

In this embodiment, an aerosol pesticidal composition of the present disclosure was prepared. The ingredients and amounts used to prepare the composition are set forth in Table 10 below.

TABLE 10

| Ingredient | Amount (wt/wt %) |
|---|---|
| Mineral oil (PD-23, available from Chemtura) | 56.20% |
| Ethyl lactate | 14.95% |
| Isopropyl myristate | 24.00% |
| Geraniol | 2.00% |
| Carbon dioxide | 2.85% |

The composition was prepared by mixing the mineral oil, ethyl lactate, isopropyl myristate and geraniol together until homogenous. The resulting composition was placed in an aerosol can. The lid and actuator of the aerosol can were sealed onto the top of the can. The carbon dioxide was introduced into the can through the actuator to pressurize the can. The resulting product can be used as an aerosol spray pesticidal composition.

Example 9

In this example, various mineral oils and alcohols were tested to determine, for cockroaches, the $LD_{50}$ and $LD_{10}$ for each.

PD23 and PD28 mineral oils were obtained from Sonneborn LLC, Mahwah, N.J. The physical properties of these oils are shown in Table 11. Each mineral oil was tested to determine the $LD_{50}$ and $LD_{10}$ (Table 12).

TABLE 11

| PROPERTY | PD23 | PD28 | Test Method |
|---|---|---|---|
| Specific gravity 60/60 | 0.800 | 0.823 | ASTM D-287 |
| Viscosity SUS @ 100° F. (38° C.) | 34 | 39 | ASTM D-2161 |
| Viscosity cSt @ 40° C. | 2.6 | 4.2 | ASTM-D-445 |
| Pour point ° F. (° C.) | 0 (−18) | −40 (−40) | ASTM D-97 |
| Distillation range, ° F. | | | |
| Ibp | 452 | 526 | |
| 50% | 486 | 568 | |
| 95% | 514 | 614 | |
| 100% | 533 | 625 | |
| Molecular weight | 220 | 245 | |

The alcohols tested comprise C1-C14 saturated straight chain alcohols, and alcohols selected from the group consisting of isopropyl alcohol, 2-butanol, isobutyl alcohol, tertiary butyl alcohol, 2-butoxyethanol, 2-phenylethanol and diacetone alcohol. The tested alcohols were obtained from Sigma-Aldrich Corp., St. Louis, Mo. Each alcohol was tested to determine the $LD_{50}$ and $LD_{10}$ (Table 12). The dose-response mortality data were analyzed using probit analysis (PoloPlus©, LeOra Software Co., Petaluma Calif., 2003) to estimate $LD_{50}$ and $LD_{10}$ values and their 95% confidence intervals.

TABLE 12

| Test Substance (CAS number) | $LD_{50}$ mg/insect (95% CI) | $LD_{10}$ mg/insect (95% CI) | Slope (+/−SE) | n (sample size) |
|---|---|---|---|---|
| PD23-mineral oil (8042-47-5) | 1.453 (1.303-1.629) | 0.754 (0.632-0.863) | 4.500 (0.360) | 394 |
| PD28-mineral oil (8042-47-5) | 2.013 (1.916-2.105) | 1.463 (1.285-1.588) | 9.259 (1.204) | 249 |
| Methanol (67-56-1) | >7.00 | Estimated at ~3.000 | n/a | 151 |

TABLE 12-continued

| Test Substance (CAS number) | LD$_{50}$ mg/insect (95% CI) | LD$_{10}$ mg/insect (95% CI) | Slope (+/−SE) | n (sample size) |
|---|---|---|---|---|
| Ethanol (64-17-5) | 2.361 (2.084-2.659) | 1.760 (1.255-2.014) | 10.037 (1.285) | 215 |
| 1-propanol (71-23-8) | 0.557 (0.527-0.582) | 0.472 (0.414-0.504) | 17.756 (2.034) | 248 |
| 1-butanol (71-36-3) | 1.018 (0.980-1.070) | 0.877 (0.814-0.917) | 19.808 (3.556) | 143 |
| 1-hexanol (111-27-3) | 0.718 (0.651-0.793) | 0.452 (0.371-0.514) | 6.392 (0.869) | 157 |
| 1-heptanol (111-70-6) | 0.791 (0.704-0.899) | 0.462 (0.324-0.549) | 5.502 (0.951) | 154 |
| 1-octanol (111-87-5) | 0.524 (0.390-0.635) | 0.267 (0.116-0.367) | 4.375 (0.720) | 149 |
| 1-nonanol (143-08-08) | 0.448 (0.296-0.633) | 0.207 (0.051-0.309) | 3.832 (0.757) | 84 |
| 1-decanol (112-30-1) | 0.421 ((0.365-0.479) | 0.275 (0.151-0.331) | 6.931 (1.023) | 272 |
| 1-undecanol (112-42-5) | 0.406 (0.373-0.444) | 0.265 (0.221-0.298) | 6.956 (1.013) | 165 |
| 1-dodecanol (112-53-8) | 0.357 (0.304-0.412) | 0.245 (0.146-0.292) | 7.809 (1.350) | 135 |
| 1-tetradecanol (112-72-1) | 1.745 (1.568-1.948) | 1.193 (0.902-1.369) | 7.756 (1.268) | 131 |
| Isopropyl alcohol (67-63-0) | 1.172 (1.014-1.394) | 0.676 (0.462-0.814) | 5.370 (0.701) | 195 |
| 2-butanol (78-92-2) | 1.188 (1.058-1.369) | 0.881 (0.709-0.997) | 9.873 (1.479) | 111 |
| isobutyl alcohol (78-83-1) | 0.517 (0.426-0.644) | 0.253 (0.146-0.326) | 4.129 (0.452) | 299 |
| tertiary butyl alcohol (75-65-0) | 0.716 (0.634-1.004) | 0.553 (0.385-0.625) | 11.392 (2.147) | 112 |
| 2-butoxyethanol (111-76-2) | 0.377 (0.349-0.413) | 0.256 (0.217-0.282) | 7.613 (1.200) | 157 |
| 2-phenylethanol (60-12-8) | 0.169 (0.114-0.327) | 0.075 (0.015-0.113) | 3.628 (0.546) | 142 |
| Diacetone alcohol (123-42-2) | 0.483 (0.390-0.591) | 0.255 (0.151-0.329) | 4.617 (0.596) | 171 |

Example 10

In this example, the effectiveness of compositions comprising various alcohols and/or mineral oil at killing cockroaches was tested.

The compositions comprising alcohol and/or mineral oil are described in Table 13. The tests were performed as described in Example 1.

TABLE 13

| Composition | # treated | # dead at 24 h | Proportion dead at 24 h |
|---|---|---|---|
| diacetone alcohol (0.4 mg) + PD23 (0.4 mg) | 11 | 11 | 1.000 |
| diacetone alcohol (0.4 mg) + PD23 (0.4 mg) | 11 | 10 | 0.909 |
| diacetone alcohol (0.4 mg) + PD23 (0.4 mg) | 12 | 11 | 0.917 |
| diacetone alcohol (0.3 mg) + PD23 (0.4 mg) | 13 | 12 | 0.923 |
| diacetone alcohol (0.3 mg) + PD23 (0.4 mg) | 13 | 11 | 0.846 |
| diacetone alcohol (0.3 mg) + PD23 (0.4 mg) | 14 | 12 | 0.857 |
| diacetone alcohol (0.3 mg) | 13 | 0 | 0.000 |
| diacetone alcohol (0.3 mg) | 13 | 0 | 0.000 |
| diacetone alcohol (0.3 mg) | 14 | 1 | 0.071 |
| methanol (1.0 mg) + PD23 (0.4 mg) | 14 | 1 | 0.071 |
| methanol (1.0 mg) + PD23 (0.4 mg) | 14 | 0 | 0.000 |
| methanol (1.0 mg) + PD23 (0.4 mg) | 14 | 1 | 0.071 |
| methanol (3.0 mg) + PD23 (0.4 mg) | 12 | 4 | 0.333 |
| methanol (3.0 mg) + PD23 (0.4 mg) | 14 | 4 | 0.286 |
| methanol (3.0 mg) + PD23 (0.4 mg) | 12 | 5 | 0.417 |
| methanol (3.0 mg) | 14 | 0 | 0.000 |
| methanol (3.0 mg) | 12 | 0 | 0.000 |
| methanol (3.0 mg) | 13 | 1 | 0.077 |
| ethanol (1.0 mg) + PD23 (0.4 mg) | 14 | 1 | 0.071 |
| ethanol (1.0 mg) + PD23 (0.4 mg) | 13 | 2 | 0.154 |
| ethanol (1.0 mg) + PD23 (0.4 mg) | 13 | 4 | 0.308 |
| ethanol (1.25 mg) + PD23 (0.4 mg) | 12 | 5 | 0.417 |
| ethanol (1.25 mg) + PD23 (0.4 mg) | 12 | 3 | 0.250 |
| ethanol (1.25 mg) + PD23 (0.4 mg) | 13 | 3 | 0.231 |
| ethanol (1.25 mg) | 13 | 0 | 0.000 |
| ethanol (1.25 mg) | 12 | 1 | 0.083 |
| ethanol (1.25 mg) | 12 | 0 | 0.000 |
| 1-propanol (0.6 mg) + PD23 (0.40 mg) | 12 | 12 | 1.000 |
| 1-propanol (0.6 mg) + PD23 (0.40 mg) | 11 | 11 | 1.000 |
| 1-propanol (0.6 mg) + PD23 (0.40 mg) | 10 | 10 | 1.000 |
| 1-propanol (0.50 mg) + PD23 (0.40 mg) | 12 | 12 | 1.000 |
| 1-propanol (0.50 mg) + PD23 (0.40 mg) | 13 | 13 | 1.000 |
| 1-propanol (0.50 mg) + PD23 (0.40 mg) | 13 | 13 | 1.000 |
| 1-propanol (0.45 mg) + PD23 (0.40 mg) | 12 | 10 | 0.833 |
| 1-propanol (0.45 mg) + PD23 (0.40 mg) | 13 | 13 | 1.000 |
| 1-propanol (0.45 mg) + PD23 (0.40 mg) | 12 | 12 | 1.000 |
| 1-propanol (0.45 mg) | 12 | 1 | 0.083 |
| 1-propanol (0.45 mg) | 12 | 0 | 0.000 |
| 1-propanol (0.45 mg) | 12 | 0 | 0.000 |
| Isopropyl alcohol (0.6 mg) + PD23 (0.4 mg) | 12 | 3 | 0.250 |
| Isopropyl alcohol (0.6 mg) + PD23 (0.4 mg) | 14 | 4 | 0.286 |
| Isopropyl alcohol (0.6 mg) + PD23 (0.4 mg) | 12 | 3 | 0.250 |
| Isopropyl alcohol (0.6 mg) | 12 | 0 | 0.000 |
| Isopropyl alcohol (0.6 mg) | 14 | 0 | 0.000 |
| Isopropyl alcohol (0.6 mg) | 12 | 0 | 0.000 |
| Isopropyl alcohol (0.8 mg) + PD23 (0.4 mg) | 12 | 3 | 0.250 |
| Isopropyl alcohol (0.8 mg) + PD23 (0.4 mg) | 13 | 7 | 0.538 |
| Isopropyl alcohol (0.8 mg) + PD23 (0.4 mg) | 12 | 10 | 0.833 |

TABLE 13-continued

| Composition | # treated | # dead at 24 h | Proportion dead at 24 h |
|---|---|---|---|
| 1-butanol (0.8 mg) + PD23 (0.4 mg) | 13 | 8 | 0.615 |
| 1-butanol (0.8 mg) + PD23 (0.4 mg) | 13 | 10 | 0.769 |
| 1-butanol (0.8 mg) + PD23 (0.4 mg) | 13 | 10 | 0.769 |
| 1-butanol (0.8 mg) | 12 | 0 | 0.000 |
| 1-butanol (0.8 mg) | 13 | 0 | 0.000 |
| 1-butanol (0.8 mg) | 10 | 1 | 0.100 |
| 2-butanol (0.8 mg) + PD23 (0.4 mg) | 12 | 1 | 0.083 |
| 2-butanol (0.8 mg) + PD23 (0.4 mg) | 14 | 0 | 0.000 |
| 2-butanol (0.8 mg) + PD23 (0.4 mg) | 12 | 3 | 0.250 |
| 2-butanol (0.8 mg) | 13 | 0 | 0.000 |
| 2-butanol (0.8 mg) | 13 | 0 | 0.000 |
| 2-butanol (0.8 mg) | 12 | 1 | 0.083 |
| t-butyl alcohol (0.5 mg) + PD23 (0.4 mg) | 10 | 3 | 0.300 |
| t-butyl alcohol (0.5 mg) + PD23 (0.4 mg) | 11 | 3 | 0.273 |
| t-butyl alcohol (0.5 mg) + PD23 (0.4 mg) | 12 | 8 | 0.667 |
| t-butyl alcohol (0.5 mg) | 12 | 0 | 0.000 |
| t-butyl alcohol (0.5 mg) | 11 | 0 | 0.000 |
| t-butyl alcohol (0.5 mg) | 10 | 0 | 0.000 |
| t-butyl alcohol (0.5 mg) | 11 | 2 | 0.182 |
| isobutyl alcohol (0.50 mg) + PD23 (0.40 mg) | 14 | 11 | 0.786 |
| isobutyl alcohol (0.50 mg) + PD23 (0.40 mg) | 13 | 13 | 1.000 |
| isobutyl alcohol (0.50 mg) + PD23 (0.40 mg) | 15 | 15 | 1.000 |
| isobutyl alcohol (0.50 mg) | 14 | 1 | 0.071 |
| isobutyl alcohol (0.20 mg) | 13 | 0 | 0.000 |
| isobutyl alcohol (0.20 mg) | 12 | 0 | 0.000 |
| isobutyl alcohol (0.20 mg) | 13 | 1 | 0.077 |
| isobutyl alcohol (0.20 mg) + PD23 (0.40 mg) | 14 | 2 | 0.143 |
| isobutyl alcohol (0.20 mg) + PD23 (0.40 mg) | 13 | 3 | 0.231 |
| isobutyl alcohol (0.20 mg) + PD23 (0.40 mg) | 15 | 11 | 0.733 |
| isobutyl alcohol (0.20 mg) + PD23 (0.40 mg) | 12 | 7 | 0.583 |
| 1-hexanol (0.4 mg) + PD23 (0.40 mg) | 13 | 13 | 1.000 |
| 1-hexanol (0.4 mg) + PD23 (0.40 mg) | 12 | 12 | 1.000 |
| 1-hexanol (0.4 mg) + PD23 (0.40 mg) | 12 | 12 | 1.000 |
| 1-hexanol (0.4 mg) | 12 | 1 | 0.083 |
| 1-hexanol (0.4 mg) | 12 | 1 | 0.083 |
| 1-hexanol (0.4 mg) | 12 | 1 | 0.083 |
| 1-heptanol (0.4 mg) + PD23 (0.40 mg) | 12 | 12 | 1.000 |
| 1-heptanol (0.4 mg) + PD23 (0.40 mg) | 12 | 11 | 0.917 |
| 1-hexanol (0.4 mg) + PD23 (0.40 mg) | 12 | 12 | 1.000 |
| 1-heptanol (0.4 mg) | 12 | 1 | 0.083 |
| 1-heptanol (0.4 mg) | 12 | 0 | 0.000 |
| 1-heptanol (0.4 mg) | 12 | 0 | 0.000 |
| 1-octanol (0.2 mg) + PD23 (0.40 mg) | 12 | 3 | 0.250 |
| 1-octanol (0.2 mg) + PD23 (0.40 mg) | 12 | 3 | 0.250 |
| 1-octanol (0.2 mg) + PD23 (0.40 mg) | 12 | 3 | 0.250 |
| 1-octanol (0.2 mg) | 13 | 2 | 0.154 |
| 1-octanol (0.2 mg) | 12 | 0 | 0.000 |
| 1-octanol (0.2 mg) | 12 | 0 | 0.000 |
| 1-nonanol (0.2 mg) + PD23 (0.40 mg) | 12 | 4 | 0.333 |
| 1-nonanol (0.2 mg) + PD23 (0.40 mg) | 12 | 3 | 0.250 |
| 1-nonanol (0.2 mg) + PD23 (0.40 mg) | 12 | 1 | 0.083 |
| 1-nonanol (0.2 mg) | 12 | 0 | 0.000 |
| 1-nonanol (0.2 mg) | 16 | 1 | 0.063 |
| 1-nonanol (0.2 mg) | 13 | 0 | 0.000 |
| 1-decanol (0.2 mg) + PD23 (0.40 mg) | 12 | 0 | 0.000 |
| 1-decanol (0.2 mg) + PD23 (0.40 mg) | 12 | 1 | 0.083 |
| 1-decanol (0.2 mg) + PD23 (0.40 mg) | 12 | 0 | 0.000 |
| 1-decanol (0.2 mg) | 12 | 0 | 0.000 |
| 1-decanol (0.2 mg) | 12 | 0 | 0.000 |
| 1-decanol (0.2 mg) | 13 | 1 | 0.077 |
| 1-undecanol (0.25 mg) + PD23 (0.40 mg) | 12 | 0 | 0.000 |
| 1-undecanol (0.25 mg) + PD23 (0.40 mg) | 13 | 1 | 0.077 |
| 1-undecanol (0.25 mg) + PD23 (0.40 mg) | 12 | 0 | 0.000 |
| 1-undecanol (0.25 mg) | 13 | 2 | 0.154 |
| 1-undecanol (0.25 mg) | 12 | 0 | 0.000 |
| 1-undecanol (0.25 mg) | 13 | 2 | 0.154 |
| 1-dodecanol (0.2 mg) + PD23 (0.40 mg) | 13 | 2 | 0.154 |
| 1-dodecanol (0.2 mg) + PD23 (0.40 mg) | 12 | 3 | 0.250 |
| 1-dodecanol (0.2 mg) + PD23 (0.40 mg) | 12 | 5 | 0.417 |
| 1-dodecanol (0.2 mg) | 13 | 2 | 0.154 |
| 1-dodecanol (0.2 mg) | 13 | 0 | 0.000 |
| 1-dodecanol (0.2 mg) | 13 | 1 | 0.077 |
| 1-tetradecanol (1.00 mg) + PD23 (0.40 mg) | 12 | 1 | 0.083 |
| 1-tetradecanol (1.00 mg) + PD23 (0.40 mg) | 12 | 0 | 0.000 |
| 1-tetradecanol (1.00 mg) + PD23 (0.40 mg) | 12 | 1 | 0.083 |
| 1-tetradecanol (1.00 mg) | 12 | 1 | 0.083 |
| 1-tetradecanol (1.00 mg) | 12 | 1 | 0.083 |
| 1-tetradecanol (1.00 mg) | 13 | 2 | 0.154 |
| 2-phenylethanol (0.1 mg) + PD23 (0.4 mg) | 12 | 7 | 0.583 |
| 2-phenylethanol (0.1 mg) + PD23 (0.4 mg) | 14 | 14 | 1.000 |
| 2-phenylethanol (0.1 mg) + PD23 (0.4 mg) | 13 | 10 | 0.769 |
| 2-phenylethanol (0.1 mg) | 12 | 1 | 0.083 |
| 2-phenylethanol (0.1 mg) | 12 | 1 | 0.083 |
| 2-phenylethanol (0.1 mg) | 13 | 0 | 0.000 |
| 2-phenylethanol (0.1 mg) | 10 | 3 | 0.300 |
| 2-butyoxyethanol (0.3 mg) + PD23 (0.4 mg) | 12 | 12 | 1.000 |
| 2-butyoxyethanol (0.3 mg) + PD23 (0.4 mg) | 12 | 12 | 1.000 |
| 2-butyoxyethanol (0.3 mg) + PD23 (0.4 mg) | 12 | 12 | 1.000 |
| 2-butyoxyethanol (0.2 mg) + PD23 (0.4 mg) | 13 | 6 | 0.462 |
| 2-butyoxyethanol (0.2 mg) + PD23 (0.4 mg) | 13 | 6 | 0.462 |
| 2-butyoxyethanol (0.2 mg) + PD23 (0.4 mg) | 13 | 2 | 0.154 |
| 2-butyoxyethanol (0.2 mg) | 14 | 0 | 0.000 |
| 2-butyoxyethanol (0.2 mg) | 13 | 0 | 0.000 |
| 2-butyoxyethanol (0.2 mg) | 13 | 0 | 0.000 |

The composite data for certain compositions is presented below (Table 14), also including the calculated proportion of cockroaches dead at 24 hours for the group treated with alcohol alone and for the group treated with the composition comprising PD23 and alcohol. The difference between the proportion of dead cockroaches in the group treated with the composition comprising PD23 and alcohol and the group treated with alcohol alone was calculated, and is also presented in Table 14. Here, the increase in mortality indicates a synergistic effect with the combination compared to the alcohol or mineral oil alone, with a higher difference indicating a greater synergy. The straight chain saturated alcohols with chain lengths of C3-C7 demonstrated the greatest increase, or difference, in mortality when combined with PD23 mineral oil, as compared to the other alcohols tested.

TABLE 14

| Individual or combination treatment | Total # cockroaches treated | # dead at 24 h | Proportion dead at 24 h | Difference (combination-alcohol) | Significance (* p < 0.05; ** p < 0.01; ns = not significant) |
|---|---|---|---|---|---|
| PD23 - mineral oil (0.40 mg) | 91 | 0 | 0 | n/a | |
| methanol (3.0 mg) | 39 | 1 | 0.026 | | |
| methanol (3.0 mg) + PD23 (0.40 mg) | 38 | 13 | 0.342 | 0.316 | * |
| ethanol (1.25 mg) | 37 | 1 | 0.027 | | |
| ethanol (1.25 mg) + PD23 (0.40 mg) | 37 | 11 | 0.297 | 0.270 | * |

TABLE 14-continued

| Individual or combination treatment | Total # cockroaches treated | # dead at 24 h | Proportion dead at 24 h | Difference (combination- alcohol) | Significance (* $p < 0.05$; ** $p < 0.01$; ns = not significant) |
|---|---|---|---|---|---|
| 1-propanol (0.45 mg) | 36 | 1 | 0.028 | | |
| 1-propanol (0.45 mg) + PD23 (0.40 mg) | 37 | 35 | 0.946 | 0.918 | ** |
| 1-butanol (0.8 mg) | 35 | 1 | 0.029 | | |
| 1-butanol (0.8 mg) + PD23 (0.40 mg) | 39 | 28 | 0.718 | 0.689 | ** |
| 1-hexanol (0.4 mg) | 36 | 3 | 0.083 | | |
| 1-hexanol (0.4 mg) + PD23 (0.40 mg) | 37 | 37 | 1.000 | 0.917 | ** |
| 1-heptanol (0.4 mg) | 36 | 1 | 0.028 | | |
| 1-heptanol (0.4 mg) + PD23 (0.40 mg) | 36 | 35 | 0.972 | 0.944 | ** |
| 1-octanol (0.2 mg) | 37 | 2 | 0.054 | | |
| 1-octanol (0.2 mg) + PD23 (0.40 mg) | 36 | 9 | 0.250 | 0.196 | * |
| 1-nonanol (0.2 mg) | 41 | 1 | 0.024 | | |
| 1-nonanol (0.2 mg) + PD23 (0.40 mg) | 36 | 8 | 0.222 | 0.198 | * |
| 1-decanol (0.2 mg) | 37 | 1 | 0.027 | | |
| 1-decanol (0.2 mg) + PD23 (0.40 mg) | 36 | 1 | 0.028 | 0.001 | ns |
| 1-undecanol (0.25 mg) | 38 | 4 | 0.105 | | |
| 1-undecanol (0.25 mg) + PD23 (0.40 mg) | 37 | 1 | 0.027 | −0.078 | ns |
| 1-dodecanol (0.2 mg) | 39 | 3 | 0.077 | | |
| 1-dodecanol (0.2 mg) + PD23 (0.40 mg) | 37 | 10 | 0.270 | 0.193 | ns |
| 1-tetradecanol (1.0 mg) | 37 | 4 | 0.108 | | |
| 1-tetradecanol (1.0 mg) + PD23 (0.40 mg) | 36 | 2 | 0.056 | −0.052 | ns |
| diacetone alcohol (0.30 mg) | 40 | 1 | 0.025 | | |
| diacetone alcohol (0.30 mg) + PD23 (0.40 mg) | 40 | 35 | 0.875 | 0.850 | ** |
| Isopropyl alcohol (0.60 mg) | 38 | 0 | 0.000 | | |
| Isopropyl alcohol (0.60 mg) + PD23 (0.40 mg) | 38 | 10 | 0.263 | 0.263 | * |
| 2-butanol (0.80 mg) | 38 | 1 | 0.026 | | |
| 2-butanol (0.80 mg) + PD23 (0.40 mg) | 38 | 4 | 0.105 | 0.079 | ns |
| t-butyl alcohol (0.50 mg) | 44 | 2 | 0.045 | | |
| t-butyl alcohol (0.50 mg) + PD23 (0.40 mg) | 33 | 14 | 0.424 | 0.379 | * |
| isobutyl alcohol (0.20 mg) | 38 | 1 | 0.026 | | |
| isobutyl alcohol (0.20 mg) + PD23 (0.40 mg) | 38 | 23 | 0.605 | 0.579 | ** |
| 2-phenylethanol (0.10 mg) | 47 | 5 | 0.106 | | |
| 2-phenylethanol (0.10 mg) + PD23 (0.40 mg) | 39 | 31 | 0.795 | 0.689 | ** |
| 2-butyoxyethanol (0.20 mg) | 40 | 0 | 0.000 | | |
| 2-butyoxyethanol (0.20 mg) + PD23 (0.40 mg) | 36 | 14 | 0.389 | 0.389 | * |

Example 11

In this embodiment, an aerosol pesticidal composition of the present disclosure was prepared. The ingredients and amounts used to prepare the composition are set forth in Table 15 below.

TABLE 15

| Ingredient | Amount (wt/wt %) |
|---|---|
| Mineral oil (PD-23, available from Chemtura) | 43.13% |
| Ethyl lactate | 14.95% |
| Isopropyl myristate | 30.00% |
| Geraniol | 6.00% |
| Nerol | 2.57% |
| Lemongrass oil | 0.50% |
| Carbon dioxide | 2.85% |

The composition was prepared by mixing a geraniol/nerol composition with the mineral oil, ethyl lactate, isopropyl myristate and lemongrass oil until homogenous. The resulting composition was placed in an aerosol can. The lid and actuator of the aerosol can were sealed onto the top of the can. The carbon dioxide was introduced into the can through the actuator to pressurize the can. The resulting product can be used as an aerosol pesticidal composition.

Example 12

In this example, the effectiveness of compositions comprising various compounds and/or mineral oil at killing cockroaches was tested.

The compounds tested are shown in Table 16. The tests were performed as described in Example 1.

TABLE 16

| Composition | # treated | # dead at 24 h | Proportion dead at 24 hr |
|---|---|---|---|
| gamma butyrolactone (96-48-0) (0.25 mg) | 7 | 3 | 0.429 |
| gamma butyrolactone (96-48-0) (0.25 mg) | 10 | 3 | 0.300 |
| gamma butyrolactone (96-48-0) (0.25 mg) | 10 | 5 | 0.500 |
| gamma butyrolactone (0.25 mg) + PD23 (0.40 mg) | 8 | 8 | 1.000 |
| gamma butyrolactone (0.25 mg) + PD23 (0.40 mg) | 10 | 9 | 0.900 |
| gamma butyrolactone (0.25 mg) + PD23 (0.40 mg) | 11 | 10 | 0.909 |
| nitromethane (75-52-5) (0.70 mg) | 11 | 0 | 0.000 |
| nitromethane (75-52-5) (0.70 mg) | 12 | 0 | 0.000 |
| nitromethane (75-52-5) (0.70 mg) | 11 | 0 | 0.000 |
| nitromethane (75-52-5) (0.80 mg) | 7 | 0 | 0.000 |
| nitromethane (75-52-5) (0.80 mg) | 10 | 2 | 0.200 |
| nitromethane (75-52-5) (0.80 mg) | 11 | 3 | 0.273 |
| Nitromethane (0.70 mg) + PD23 (0.40 mg) | 11 | 6 | 0.545 |
| Nitromethane (0.70 mg) + PD23 (0.40 mg) | 11 | 7 | 0.636 |
| Nitromethane (0.70 mg) + PD23 (0.40 mg) | 11 | 7 | 0.636 |
| Nitromethane (0.80 mg) + PD23 (0.40 mg) | 7 | 7 | 1.000 |
| Nitromethane (0.80 mg) + PD23 (0.40 mg) | 10 | 9 | 0.900 |
| Nitromethane (0.80 mg) + PD23 (0.40 mg) | 11 | 7 | 0.636 |
| Di(ethylene) glycol (111-46-6) (0.80 mg) | 10 | 0 | 0.000 |
| Di(ethylene) glycol (111-46-6) (0.80 mg) | 10 | 0 | 0.000 |
| Di(ethylene) glycol (111-46-6) (0.80 mg) | 13 | 6 | 0.462 |
| Di(ethylene) glycol (0.80 mg) + PD23 (0.40 mg) | 10 | 0 | 0.000 |
| Acetophenone (98-86-2) (0.10 mg) | 10 | 0 | 0.000 |
| Acetophenone (98-86-2) (0.10 mg) | 10 | 0 | 0.000 |
| Acetophenone (98-86-2) (0.10 mg) | 10 | 0 | 0.000 |
| Acetophenone (98-86-2) (0.10 mg) + PD23 (0.40 mg) | 10 | 3 | 0.300 |
| Acetophenone (98-86-2) (0.10 mg) + PD23 (0.40 mg) | 10 | 8 | 0.800 |
| Acetophenone (98-86-2) (0.10 mg) + PD23 (0.40 mg) | 10 | 10 | 1.000 |
| diethyl ether (60-29-7) (2.00 mg) | 11 | 0 | 0.000 |
| diethyl ether (60-29-7) (2.00 mg) | 10 | 0 | 0.000 |
| diethyl ether (2.00 mg) + PD23 (0.40 mg) | 10 | 1 | 0.000 |
| Isopropyl acetate (108-21-4) (1.00 mg) | 10 | 1 | 0.100 |
| Isopropyl acetate (108-21-4) (1.00 mg) | 10 | 2 | 0.200 |
| Isopropyl acetate (108-21-4) (1.00 mg) + PD23 (0.40 mg) | 10 | 0 | 0.000 |
| 2-butanone (methyl ethyl ketone) (78-93-3) (2.00 mg) | 13 | 0 | 0.000 |
| 2-butanone (methyl ethyl ketone) (78-93-3) (2.00 mg) | 12 | 2 | 0.167 |
| 2-butanone (methyl ethyl ketone) (78-93-3) (2.00 mg) | 11 | 1 | 0.091 |
| 2-butanone (methyl ethyl ketone) (78-93-3) (2.00 mg) + PD23 (0.40 mg) | 10 | 3 | 0.300 |
| 2-butanone (methyl ethyl ketone) (78-93-3) (2.00 mg) + PD23 (0.40 mg) | 12 | 2 | 0.167 |
| 2-butanone (methyl ethyl ketone) (78-93-3) (2.00 mg) + PD23 (0.40 mg) | 12 | 2 | 0.167 |
| Triacetin (102-76-1) (2.00 mg) | 10 | 0 | 0.000 |
| Triacetin (102-76-1) (2.00 mg) | 10 | 1 | 0.100 |
| Triacetin (102-76-1) (2.00 mg) | 10 | 0 | 0.000 |
| Triacetin (102-76-1) (2.0 mg) + PD23 (0.40 mg) | 11 | 6 | 0.545 |
| Triacetin (102-76-1) (2.0 mg) + PD23 (0.40 mg) | 10 | 8 | 0.800 |
| Triacetin (102-76-1) (2.0 mg) + PD23 (0.40 mg) | 10 | 8 | 0.800 |
| Pyridine (110-86-1) (0.10 mg) | 11 | 0 | 0.000 |
| Pyridine (110-86-1) (0.10 mg) | 10 | 0 | 0.000 |
| Pyridine (110-86-1) (0.10 mg) | 10 | 1 | 0.100 |
| Pyridine (110-86-1) (0.10 mg) + PD23 (0.40 mg) | 10 | 10 | 1.000 |
| Pyridine (110-86-1) (0.10 mg) + PD23 (0.40 mg) | 10 | 10 | 1.000 |
| Pyridine (110-86-1) (0.10 mg) + PD23 (0.40 mg) | 10 | 10 | 1.000 |
| Chloroform anhydrous (67-66-3) (1.00 mg) | 10 | 1 | 0.100 |
| Chloroform anhydrous (67-66-3) (1.00 mg) | 10 | 0 | 0.000 |
| Chloroform anhydrous (67-66-3) (1.00 mg) + PD23 (0.40 mg) | 10 | 0 | 0.000 |
| Methyl isobutyl ketone (108-10-1) (1.00 mg) | 10 | 1 | 0.100 |
| Methyl isobutyl ketone (108-10-1) (1.00 mg) | 11 | 0 | 0.000 |
| Methyl isobutyl ketone (108-10-1) (1.00 mg) + PD23 (0.40 mg) | 10 | 1 | 0.100 |
| Tetrahydrofuran (109-99-9) (0.80 mg) | 10 | 3 | 0.300 |
| Tetrahydrofuran (109-99-9) (0.80 mg) + PD 23 (0.40 mg) | 10 | 0 | 0.000 |
| 2-ethoxyethanol (ethyl cellosolve) (110-80-5) (0.60 mg) | 10 | 1 | 0.100 |
| 2-ethoxyethanol (ethyl cellosolve) (110-80-5) (0.60 mg) | 10 | 0 | 0.000 |

TABLE 16-continued

| Composition | # treated | # dead at 24 h | Proportion dead at 24 hr |
|---|---|---|---|
| 2-ethoxyethanol (ethyl cellosolve) (110-80-5) (0.60 mg) | 10 | 0 | 0.000 |
| 2-ethoxyethanol (ethyl cellosolve) (110-80-5) (0.60 mg) + 0.40 mg PD23 | 10 | 8 | 0.800 |
| 2-ethoxyethanol (ethyl cellosolve) (110-80-5) (0.60 mg) + 0.40 mg PD23 | 10 | 5 | 0.500 |
| 2-ethoxyethanol (ethyl cellosolve) (110-80-5) (0.60 mg) + 0.40 mg PD23 | 11 | 7 | 0.636 |
| n-methyl pyrrolidone (872-50-4) (0.10 mg) | 10 | 5 | 0.500 |
| n-methyl pyrrolidone (872-50-4) (0.05 mg) | 10 | 1 | 0.100 |
| n-methyl pyrrolidone (872-50-4) (0.10 mg) + PD23 (0.40 mg) | 10 | 7 | 0.700 |
| n-methyl pyrrolidone (872-50-4) (0.05 mg) + PD23 (0.40 mg) | 12 | 1 | 0.083 |
| Polyethylene glycol 200 Sigma (25322-68-3) (0.80 mg) | 10 | 1 | 0.100 |
| Polyethylene glycol 200 Sigma (25322-68-3) (0.80 mg) | 10 | 0 | 0.000 |
| Polyethylene glycol 200 Sigma (25322-68-3) (0.80 mg) | 12 | 4 | 0.333 |
| Polyethylene glycol 200 Sigma (0.80 mg) + PD23 (0.40 mg) | 10 | 3 | 0.300 |
| Dimethoxymethane (methylal) (109-87-5) (2.00 mg) | 12 | 0 | 0.000 |
| Dimethoxymethane (methylal) (109-87-5) (2.00 mg) | 10 | 0 | 0.000 |
| Dimethoxymethane (methylal) (109-87-5) (2.00 mg) + PD23 (0.40 mg) | 10 | 1 | 0.100 |
| Methyl chloroform (71-55-6) (2.00 mg) | 11 | 1 | 0.091 |
| Methyl chloroform (71-55-6) (2.00 mg) | 10 | 1 | 0.100 |
| Methyl chloroform (71-55-6) (2.00 mg) + PD23 (0.40 mg) | 10 | 0 | 0.000 |
| Diisopropyl biphenyl Nu-solv (69009-90-1) (0.80 mg) | 10 | 0 | 0.000 |
| Diisopropyl biphenyl Nu-solv (69009-90-1) (0.80 mg) + PD23 (0.40 mg) | 10 | 2 | 0.200 |
| Hexanes (110-54-3) (0.80 mg) | 10 | 1 | 0.100 |
| Hexanes (0.80 mg) + PD23 (0.40 mg) | 10 | 0 | 0.000 |
| Methyl t-butyl ether (1634-04-4) (2.00 mg) | 12 | 2 | 0.167 |
| Methyl t-butyl ether (1634-04-4) (2.00 mg) | 10 | 3 | 0.300 |
| Methyl t-butyl ether (1634-04-4) (2.00 mg) + PD23 (0.40 mg) | 10 | 2 | 0.200 |
| Dichloromethane (methylene chloride) (75-09-02) (1.50 mg) | 10 | 0 | 0.000 |
| Dichloromethane (methylene chloride) (1.50 mg) + PD23 (0.40 mg) | 10 | 0 | 0.000 |
| Toluene (108-88-3) (0.90 mg) | 10 | 0 | 0.000 |
| Toluene (108-88-3) (0.90 mg) + PD23 (0.40 mg) | 10 | 1 | 0.100 |

The composite data for certain compositions is presented below (Table 17), also including the calculated proportion of cockroaches dead at 24 hours for the group treated with the specific compounds alone and for the group treated with the composition comprising PD23 and the compound. The difference between the proportion of dead cockroaches in the group treated with the composition comprising PD23 and the compounds and the group treated with the compounds alone was calculated, and is also presented in Table 17. Here, the increase in mortality indicates a synergistic effect with the combination compared to the tested compound or mineral oil alone, with a higher difference indicating a greater synergy. γ-butyrolactone, nitromethane, acetophenone, triacetin, pyridine and 2-ethoxyethanol demonstrated the greatest increase in mortality when combined with PD23 mineral oil, as compared to the other compounds tested.

TABLE 17

| Individual or combination treatment | Total # of cockroaches treated | # dead at 24 h | Proportion dead at 24 h | Difference (combination-solvent) | Significance (* $p < 0.05$; ** $p < 0.01$; ns = not significant) |
|---|---|---|---|---|---|
| PD23-mineral oil (0.40 mg) | 91 | 0 | 0.000 | n/a | |
| gamma butyrolactone (96-48-0) (0.25 mg) | 27 | 11 | 0.407 | | |
| gamma butyrolactone (96-48-0) (0.25 mg) + PD23 (0.40 mg) | 29 | 27 | 0.931 | 0.524 | ** |
| nitromethane (75-52-5) (0.70 mg) | 34 | 0 | 0.000 | | |
| nitromethane (75-52-5) (0.70 mg) + PD23 (0.40 mg) | 33 | 20 | 0.606 | 0.606 | ** |
| nitromethane (75-52-5) (0.80 mg) | 28 | 5 | 0.179 | | |
| nitromethane (75-52-5) (0.80 mg) + PD23 (0.40 mg) | 28 | 23 | 0.821 | 0.643 | ** |
| Di(ethylene) glycol (111-46-6) (0.80 mg) | 33 | 6 | 0.182 | | |
| Di(ethylene) glycol (111-46-6) (0.80 mg) + PD23 (0.40 mg) | 10 | 0 | 0.000 | −0.182 | ns |
| Acetophenone (98-86-2) (0.10 mg) | 30 | 0 | 0.000 | | |

TABLE 17-continued

| Individual or combination treatment | Total # of cockroaches treated | # dead at 24 h | Proportion dead at 24 h | Difference (combination-solvent) | Significance (* p < 0.05; ** p < 0.01; ns = not significant) |
|---|---|---|---|---|---|
| Acetophenone (98-86-2) (0.10 mg) + PD23 (0.40 mg) | 30 | 21 | 0.700 | 0.700 | * |
| diethyl ether (60-29-7) (2.0 mg) | 21 | 0 | 0.000 | | |
| diethyl ether (60-29-7) (2.0 mg) + PD23 (0.40 mg) | 10 | 1 | 0.100 | 0.100 | ns |
| Isopropyl acetate (108-21-4) (1.0 mg) | 20 | 3 | 0.150 | | |
| Isopropyl acetate (108-21-4) (1.0 mg) + PD23 (0.40 mg) | 10 | 0 | 0.000 | −0.150 | ns |
| 2-butanone (methyl ethyl ketone) (78-93-3) (2.0 mg) | 36 | 3 | 0.083 | | |
| 2-butanone (methyl ethyl ketone) (78-93-3) (2.0 mg) + PD23 (0.40 mg) | 34 | 7 | 0.206 | 0.123 | ns |
| Triacetin (102-76-1) (2.0 mg) | 30 | 1 | 0.033 | | |
| Triacetin (102-76-1) (2.0 mg) + PD23 (0.40 mg) | 31 | 22 | 0.710 | 0.676 | ** |
| Pyridine (110-86-1) (0.10 mg) | 31 | 1 | 0.032 | | |
| Pyridine (110-86-1) (0.10 mg) + PD23 (0.40 mg) | 30 | 30 | 1.000 | 0.968 | ** |
| Chloroform-anhydrous (67-66-3) (2.0 mg) | 20 | 1 | 0.050 | | |
| Chloroform-anhydrous (67-66-3) (2.0 mg) + PD23 (0.40 mg) | 10 | 0 | 0.000 | −0.050 | ns |
| Methyl isobutyl ketone (108-10-1) (1.0 mg) | 21 | 1 | 0.048 | | |
| Methyl isobutyl ketone (108-10-1) (1.0 mg) + PD23 (0.40 mg) | 10 | 1 | 0.100 | 0.052 | ns |
| Tetrahydrofuran (109-99-9) (0.80 mg) | 10 | 3 | 0.300 | | |
| Tetrahydrofuran (109-99-9) (0.80 mg) + PD 23 (0.40 mg) | 10 | 0 | 0.000 | −0.300 | ns |
| 2-ethoxyethanol (ethyl cellosolve) (110-80-5) (0.60 mg) | 30 | 1 | 0.033 | | |
| 2-ethoxyethanol (ethyl cellosolve) (110-80-5) (0.60 mg) + PD23 (0.40 mg) | 31 | 20 | 0.645 | 0.612 | ** |
| n-methyl pyrrolidone (872-50-4) (0.05 mg) | 10 | 1 | 0.100 | | |
| n-methyl pyrrolidone (872-50-4) (0.05 mg) + PD23 (0.40 mg) | 12 | 1 | 0.083 | −0.017 | ns |
| n-methyl pyrrolidone (872-50-4) (0.10 mg) | 10 | 5 | 0.500 | | |
| n-methyl pyrrolidone (872-50-4) (0.10 mg) + PD23 (0.40 mg) | 10 | 7 | 0.700 | 0.200 | ns |
| Polyethylene glycol 200 Sigma (25322-68-3) (0.80 mg) | 32 | 5 | 0.156 | | |
| Polyethylene glycol 200 Sigma (25322-68-3) (0.80 mg) + PD23 (0.40 mg) | 10 | 3 | 0.300 | 0.144 | ns |
| Dimethoxymethane (methylal) (109-87-5) (2.0 mg) | 22 | 0 | 0.000 | | |
| Dimethoxymethane (methylal) (109-87-5) (2.0 mg) + PD23 (0.40 mg) | 10 | 1 | 0.100 | 0.100 | ns |
| Methyl chloroform (71-55-6) (2.00 mg) | 21 | 2 | 0.095 | | |
| Methyl chloroform (71-55-6) (2.00 mg) + PD23 (0.40 mg) | 10 | 0 | 0.000 | −0.095 | ns |

TABLE 17-continued

| Individual or combination treatment | Total # of cockroaches treated | # dead at 24 h | Proportion dead at 24 h | Difference (combination-solvent) | Significance (* p < 0.05; ** p < 0.01; ns = not significant) |
|---|---|---|---|---|---|
| Diisopropyl biphenyl Nu-solv (69009-90-1) (0.80 mg) | 10 | 0 | 0.000 | | |
| Diisopropyl biphenyl Nu-solv (69009-90-1) (0.80 mg) + PD23 (0.40 mg) | 10 | 2 | 0.200 | 0.200 | |
| Hexanes (110-54-3) (0.80 mg) | 10 | 1 | 0.100 | | |
| Hexanes (110-54-3) (0.80 mg) + PD23 (0.40 mg) | 10 | 0 | 0.000 | −0.100 | ns |
| Methyl t-butyl ether (1634-04-4) (2.00 mg) | 22 | 5 | 0.227 | | |
| Methyl t-butyl ether (1634-04-4) (2.00 mg) + PD23 (0.40 mg) | 10 | 2 | 0.200 | −0.027 | ns |
| Dichloromethane (methylene chloride) (75-09-02) (1.50 mg) | 10 | 0 | 0.000 | | |
| Dichloromethane (methylene chloride) (75-09-02) (1.50 mg) + PD23 (0.40 mg) | 10 | 0 | 0.000 | 0.000 | ns |
| Toluene (108-88-3) (0.90 mg) | 10 | 0 | 0.000 | | |
| Toluene (108-88-3) (0.90 mg) + PD23 (0.40 mg) | 10 | 1 | 0.100 | 0.100 | ns |

Example 17

1-propanol and 1-heptanol were tested alone and in combination with Exxsol D95 mineral oil. EXXSOL D95 was also tested alone. The results are shown in Table 18. Both alcohols exhibited significant synergy with EXXSOL D95.

When introducing elements of the present disclosure or the preferred embodiments(s) thereof, the articles "a", "an", "the" and "said" are intended to mean that there are one or more of the elements. The terms "comprising", "including" and "having" are intended to be inclusive and mean that there may be additional elements other than the listed elements.

In view of the above, it will be seen that the several objects of the disclosure are achieved and other advantageous results attained.

As various changes could be made in the above compositions and products without departing from the scope of the disclosure, it is intended that all matter contained in the above description shall be interpreted as illustrative and not in a limiting sense.

What is claimed is:

1. A pesticidal composition comprising at least about 10% mineral oil by weight of the composition and at least about 10% ethyl lactate by weight of the composition.

2. The composition of claim 1 wherein the composition comprises at least about 30% mineral oil by weight of the composition.

3. The composition of claim 1 wherein the composition further comprises a plant essential oil or derivative thereof.

4. The composition of claim 3 wherein the plant essential oil or derivative thereof is geraniol.

5. The composition of claim 4 wherein the composition further comprises isopropyl myristate.

6. The composition of claim 5 wherein the composition comprises, by weight of the composition, about 43% mineral oil, about 15% ethyl lactate, about 30% by weight isopropyl myristate, and about 6% geraniol.

7. The composition of claim 6 wherein the composition further comprises about 3% nerol and about 1% lemongrass oil.

TABLE 18

| Individual or combination treatment | Total # of cockroaches treated | # dead at 24 h | Proportion dead at 24 h | Difference (combination-solvent) | Significance (* p < 0.05; ** p < 0.01) |
|---|---|---|---|---|---|
| EXXSOL D95 (64742-47-8) (0.40 mg) | 30 | 1 | 0.033 | | |
| 1-heptanol (111-70-6) (0.40 mg) | 36 | 1 | 0.028 | | |
| 1-propanol (71-23-8) (0.45 mg) | 36 | 1 | 0.028 | | |
| EXXSOL D95 (0.40 mg) + 1 heptanol (0.40 mg) | 21 | 21 | 1.000 | 0.972 | ** |
| EXXSOL D95 (0.40 mg) + 1-propanol (0.40 mg) | 21 | 19 | 0.905 | 0.877 | ** |

8. The composition of claim 1 wherein the mineral oil is a petroleum distillate.

9. The composition of claim 1 wherein the composition further comprises an emulsifier.

10. The composition of claim 1 wherein the composition comprises from about 10% to about 60% ethyl lactate by weight of the composition.

* * * * *